(12) United States Patent
Chen et al.

(10) Patent No.: US 9,187,491 B2
(45) Date of Patent: Nov. 17, 2015

(54) GAMBOGENIC ACID DERIVATIVES, PREPARATION METHOD AND APPLICATION THEREOF

(71) Applicant: Ninth People's Hospital, School Medicine Shanghai Jiao Tong University, Shanghai (CN)

(72) Inventors: Wantao Chen, Shanghai (CN); Xu Wang, Shanghai (CN); Zhiyuan Zhang, Shanghai (CN); Chenping Zhang, Shanghai (CN); Li Mao, Shanghai (CN); Ping Zhang, Shanghai (CN); Qin Xu, Shanghai (CN); Ming Yan, Shanghai (CN); Jianjun Zhang, Shanghai (CN); Jinsong Pan, Shanghai (CN); Yan Lv, Shanghai (CN); Rongxin Deng, Shanghai (CN); Weiliu Qiu, Shanghai (CN)

(73) Assignee: Ninth People's Hospital, School Medicine Shanghai Jiao Tong University, Shanghai (CN)

( * ) Notice: Subject to any disclaimer, the term of this patent is extended or adjusted under 35 U.S.C. 154(b) by 0 days.

(21) Appl. No.: 14/354,839

(22) PCT Filed: Sep. 28, 2012

(86) PCT No.: PCT/CN2012/082306
§ 371 (c)(1),
(2) Date: Apr. 28, 2014

(87) PCT Pub. No.: WO2013/107189
PCT Pub. Date: Jul. 25, 2013

(65) Prior Publication Data
US 2014/0309418 A1    Oct. 16, 2014

(30) Foreign Application Priority Data

Jan. 18, 2012   (CN) .......................... 2012 1 0014980

(51) Int. Cl.
| | | |
|---|---|---|
| A61K 31/352 | (2006.01) |
| C07D 313/06 | (2006.01) |
| C07D 493/08 | (2006.01) |
| C07D 493/20 | (2006.01) |
| A61K 31/4025 | (2006.01) |
| A61K 31/453 | (2006.01) |
| C07D 519/00 | (2006.01) |
| C07D 493/18 | (2006.01) |

(52) U.S. Cl.
CPC .......... *C07D 493/08* (2013.01); *A61K 31/4025* (2013.01); *A61K 31/453* (2013.01); *C07D 493/18* (2013.01); *C07D 493/20* (2013.01); *C07D 519/00* (2013.01)

(58) Field of Classification Search
CPC ............ A61K 31/453; A61K 31/4025; A61K 31/4433; A61K 31/4178; A61K 31/5377; A61K 31/4188; A61K 31/496; A61K 31/497; A61K 31/5513; C07D 493/20; C07D 493/22; C07D 519/00
USPC .................. 549/381, 382, 510; 548/526, 953; 546/197; 544/150, 378; 540/596
See application file for complete search history.

(56) References Cited

U.S. PATENT DOCUMENTS 6,462,041 B1 * 10/2002 Cai et al. ..................... 514/232.5
7,176,234 B2 *  2/2007 Cai et al. ..................... 514/450

FOREIGN PATENT DOCUMENTS

| | | | | |
|---|---|---|---|---|
| CA | 2396005 A1 | * | 8/2000 | ........... C07D 493/22 |
| CN | 1715283 | * | 1/2004 | ........... C07D 493/22 |
| EP | 1180991 | * | 8/2000 | ........... C07D 493/22 |

OTHER PUBLICATIONS

Asano et al, Cytotoxic Xanthones from Garcinia Hanburyl, Phytochem. vol. 41,No. 3, pp. 815-820(1996).*

*Primary Examiner* — Andrew D Kosar
*Assistant Examiner* — Raymond Covington
(74) *Attorney, Agent, or Firm* — Wang Law Firm, Inc.; Li K. Wang; Stephen Hsu

(57) ABSTRACT

Gambogenic acid derivatives having a structure shown as Formula (I) or (II), salts, preparation method and application thereof in the treatment of tumor. Compared with gambogenic acid, the gambogenic acid derivatives exhibit more potent anti-tumor activities.

14 Claims, 5 Drawing Sheets

GAMBOGENIC ACID DERIVATIVES, PREPARATION METHOD AND APPLICATION THEREOF

FIELD OF THE INVENTION

The present invention relates to an antitumor drug, and its preparation method and application, in particular to gambogenic acid derivatives, their preparation and use.

BACKGROUND OF THE INVENTION

As people have longer lifespan with changes in diet habits, cancer patients have increased from year to year. WHO data shows that cancer has become a major fatal disease, and cancer patients will continue to increase; cancer as the leading cause of death in 2008 accounted for 13.8%, and is expected to account for more than 15% in 2015.

Currently, the clinical treatments of malignant tumors are primarily by surgery, radiotherapy, and chemotherapy, either alone or in combination. In recent years, the survival time of cancer patients was significantly prolonged by chemotherapy. However, existing anticancer drugs still cannot meet the clinical needs due to the high variability of tumor cells and the generation of multi-drug resistance. Cytotoxic drugs as a major component of chemotherapy in cancer treatment have played a very important role. So far, these drugs still occupy major market share of anticancer drugs, including drugs obtained from natural products, such as Taxol drugs, etc., and they become common anti-cancer drugs in clinical practices because of their therapeutic effects.

Nevertheless, cytotoxic chemotherapy drugs can cause multi-drug resistance of the tumor cells after long-term using, which reduce the efficacy of these drugs, such that doctors increase drug dosage to improve efficacy, thereby reducing drug security. Adverse reactions would be caused because cytotoxic drugs kill tumor cells while also killing normal cells. All cytotoxic drugs usually lead to adverse reactions in patients, and the adverse reactions are increasing in accordance with the increasing dosage. Therefore, the maximum dose of chemotherapeutic drug is strictly limited. In other words, it is not feasible to increase administration to improve drug efficacy when the drug resistance occur. The only feasible way is to replace another effective chemotherapy drug. Thus, more effective chemotherapy drugs shall be developed for clinicians, and the research and development of new and effective anticancer drugs is undoubtedly one of the most urgent tasks.

*Garcinia* (Gamboge) is yellow resin from gamboge trees that grow in India, Vietnam, and in Yunnan, Hunan, and Hubei areas in China, and can be used as a yellow pigment in painting. The book "Compendium of Materia Medica" authored by Li Shizhen of the Ming Dynasty cited that "*Garcinia* used for painter was decocted". *Garcinia* is one of the Chinese medicines that inhibit tumor growth and refractory carbuncle.

Gambogenic acid (as shown in Formula X, numbers representing a carbon sequence) is the active ingredient of *Garcinia*. It has been reported that gambogenic acid can inhibit tumor growth in vitro and in vivo, induce tumor cells apoptosis, and show stronger anti-tumor activities for a variety of malignant tumors due to it's characteristic of selectively inhibiting tumor growth.

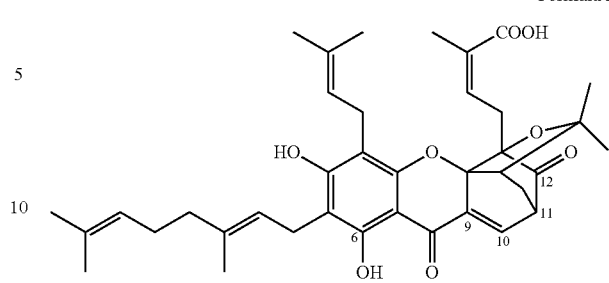

Formula X

Bao-Xi, Qu etc. (Chinese Journal of Clinical Oncology, 1991, Volume 18, No. 1, page 50) demonstrated that gambogenic acid has broad anti-cancer activities, less toxicity, and better inhibitory effect for inhibiting S180, ARS ascites carcinoma, P388 leukemia, Lewis lung cancer and La795 lung cancer. In comparison with *garcinia* acid (another anti-tumor components extracted from *Garcinia*), gambogenic acid is stronger for inhibiting mouse leukemia L1210, and the highest survival rate of gambogenic acid is extended up to 2.45 times than that of *garcinia* acid. The research results of cell cycle of L1210 leukemia show that gambogenic acid (intravenous infusion, 10 mg/kg) can inhibit G1-S phase transition by reducing S phase cells and promoting G1 phase cells.

Cheng Hui, etc. (Herbal, 2008, Volume 39 No. 2, page 236) observed proliferative inhibition of a variety of malignant cells by gambogenic acid via MTT method. The result showed that gambogenic acid can be significantly used for proliferative inhibition of human colon cancer cells (HCT-8), human hepatoma cells (BEL-7402), human gastric cancer cells (BGC-823), human non-small cell lung cancer cells (A549), and human ovarian cancer (A2780).

Gambogenic acid is a common active ingredient in traditional Chinese medicine. The extraction process of gambogenic acid is simple, low cost, and gambogenic acid can be obtained plentifully for developing anti-tumor drug.

Patent CN1718183A disclosed gambogenic acid preparation can inhibit human hepatoma BEL-7402, human hepatoma 7721, human breast cancer MCF-7, and human cervical carcinoma Hela cells, wherein the human hepatoma cells are most sensitive. Patent CN1718184A disclosed gambogenic acid complexes combined with anticancer drugs such as moroxydine, amantadine, cytarabine, and matrine for the treatment of liver cancer, colon cancer, and lung cancer due to prominent efficacy and lower irritation and toxicity. Patent CN101947204A disclosed solid lipid nanoparticles of gambogenic acid: preparing gambogenic acid to make solid nanoparticles to improve bioavailability, reduce irritation, and prolong efficacy time.

In comparison with the current clinical drugs, gambogenic acid obtained from nature has shortcomings including that the activity is not strong enough, and safe dose is small, thereby limiting its development and application. Thus, the structure of the gambogenic acid has to be modified to improve its activity and druggability.

SUMMARY OF THE INVENTION

To overcome the shortcomings that the activity of the gambogenic acid is not strong enough, the objective of the present invention is to provide a gambogenic acid derivative that has better anti-tumor activity, so as to provide leading compounds for antitumor researches or new candidate compounds for antitumor drugs.

In one aspect, the present invention is to provide a gambogenic acid derivative, the gambogenic acid derivative represented by of the molecular structure represented in any one of Formula (I) to (II):

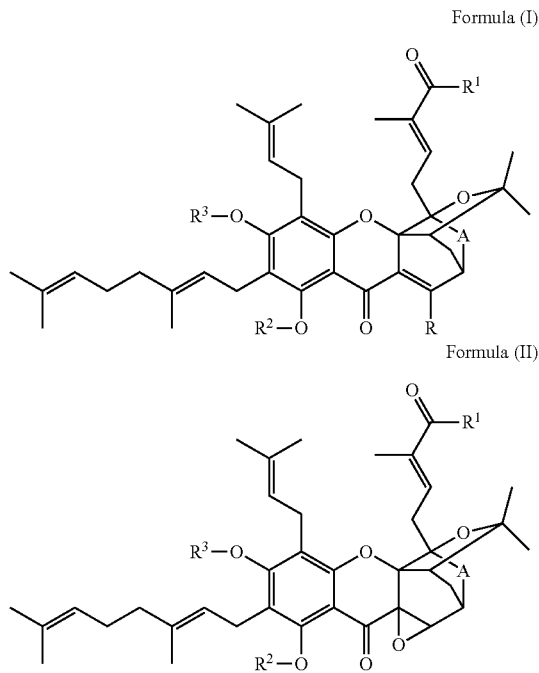

wherein A is —CO— or —HC(OH)—; $R^1$ is selected from:

1) —$OR^4$;

wherein $R^4$ is selected from the group consisting of any one of the following: hydrogen, straight chain or branched chain $C_1$ to $C_{10}$ alkyl group, or alkyl group containing optionally 1 to 3 substituted groups including oxygen group, halogen, $C_1$ to $C_{10}$ alkoxy group, acyloxy group, $C_1$ to $C_{10}$ alkoxycarbonyl group, aryloxy group; $C_3$-$C_8$ cycloalkyl group, $C_1$ to $C_{10}$ alkyl group substituted by 1, 2 or 3 heteroatoms; alkylaryl group including $C_1$ to $C_{10}$ alkyl group substituted by aromatic group and $C_1$ to $C_{10}$ alkyl group optionally substituted by 1 to 3 substituted aromatic groups including acyl group, —$OCH_2O$—, halogen, haloalkyl group, aryl group, $C_3$ to $C_8$ cycloalkyl group, $C_1$ to $C_{10}$ alkyl group, hydroxyl group, acyloxy group, $C_1$ to $C_{10}$ alkoxy group; heteroarylalkyl group including $C_1$ to $C_{10}$ alkoxy group substituted by heteroaryl group, and $C_1$ to $C_{10}$ alkyl group optionally substituted by any heteroaryl group including heteroaryl group, $C_1$ to $C_{10}$ alkyl group, aralkyl group, $C_3$ to $C_8$ cycloalkyl group, $C_1$ to $C_{10}$ alkoxycarbonyl group, carbamoyl group, aromatic group and $C_1$ to $C_6$ amide group; straight chain or branched chain $C_2$ to $C_{10}$ alkenyl group or alkynyl group including optionally 1 to 3 substituted groups including oxygen group, halogen, aromatic ring group, aralkyl group, $C_1$ to $C_{10}$ alkoxy group, acyloxy group, amide group, $C_1$ to $C_6$ amine acyl group, $C_1$ to $C_{10}$ alkoxy group and $C_1$ to $C_{10}$ heteroalkyl group including 1, 2 or 3 heteroatoms; $C_4$ to $C_{10}$ cycloalkenyl, $C_4$ to $C_{10}$ alkynyl group, or alkynyl group including optionally 1 to 3 substituted groups including oxygen group, halogen, aromatic ring group, aralkyl group, $C_1$ to $C_{10}$ alkoxy group, acyloxy group, amide group, $C_1$ to $C_6$ acyl group, $C_1$ to $C_{10}$ alkoxy group, aryloxy group and $C_1$ to $C_{10}$ heteroalkyl group including optionally 1, 2 or 3 heteroatoms.

2) —$NR^5R^6$;

wherein $R^5$ and $R^6$ may be identical or different, and are independently selected from any one of the substituted groups as follows: hydrogen; straight chain or branched $C_1$ to $C_{10}$ alkyl group or $C_1$ to $C_{10}$ alkyl group containing optionally 1 to 3 substituted groups including oxygen group, halogen, $C_1$ to $C_{10}$ alkoxy group, acyloxy group, $C_1$ to $C_{10}$ alkoxyacyl group, aryloxy group; $C_3$ to $C_8$ cycloalkyl group; $C_1$ to $C_{10}$ alkyl group substituted by 1, 2 or 3 heteroatoms; alkylaryl group including $C_1$ to $C_{10}$ alkyl group substituted by aromatic group and $C_1$ to $C_{10}$ alkyl group substituted by optionally 1 to 3 substituted aromatic groups including acyl group, —$OCH_2O$—, halogen, haloalkyl group, hydroxyl group, aryl group, $C_3$ to $C_8$ cycloalkyl group, $C_1$ to $C_{10}$ alkyl group, acyloxy group, $C_1$ to $C_{10}$ alkoxy group; heteroarylalkyl group including $C_1$ to $C_{10}$ alkoxy group substituted by heteroaryl group, and $C_1$ to $C_{10}$ alkyl group optionally substituted by any heteroaryl group including heteroaryl group, $C_1$ to $C_{10}$ alkyl group, aralkyl group, $C_3$ to $C_8$ cycloalkyl group, $C_1$ to $C_{10}$ alkoxycarbonyl group, carbamoyl group, aromatic group and $C_1$ to $C_6$ amide group; straight chain or branched chain $C_2$ to $C_{10}$ alkenyl group or alkenyl group containing optionally 1 to 3 substituted groups including oxygen group, halogen, aromatic ring group, aralkyl group, $C_1$ to $C_{10}$ alkoxy group, acyloxy group, amide group, $C_1$ to $C_6$ amine acyl group, $C_1$ to $C_{10}$ alkoxy group, aryloxy group and $C_1$ to $C_{10}$ heteroalkyl group containing 1, 2 or 3 heteroatoms; $C_4$ to $C_{10}$ cycloalkenyl, $C_4$ to $C_{10}$ alkynyl group, or alkynyl group containing optionally 1 to 3 substituted groups including oxygen group, halogen, aromatic ring group, aralkyl group, $C_1$ to $C_{10}$ alkoxy group, acyloxy group, amide group, $C_1$ to $C_6$ acyl group, $C_1$ to $C_{10}$ alkoxy group, aryloxy group and $C_1$ to $C_{10}$ heteroalkyl group including 1, 2 or 3 heteroatoms.

3)

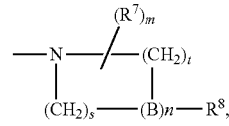

wherein s and t are positive integers, and the sum of s and t is a natural number of 2 to 10;

m is 0, 1, 2 or 3, and represents the number of the substituted group on $R^7$ of the ring;

n is 0, 1, 2 or 3, and represents the number of B on the ring; B is carbon, nitrogen or oxygen;

the groups of $R^7$, $R^8$ are identical with the group of $R^5$, or carbonyl group, imino group, oxime group, aliphatic group; or when B is tertiary nitrogen, $R^8$ is oxygen, and so as to form nitrogen oxides with B;

$R^2$ is selected from any one of the substituted groups as follows: hydrogen, straight chain or branched chain $C_1$ to $C_{10}$ alkyl group, $C_3$ to $C_8$ cycloalkyl group, aromatic group or aromatic group substituted by $C_1$ to $C_{10}$ alkyl, heteroaryl group, and acyl group substituted by $C_1$ to $C_{10}$ alkyl or acyl group substituted by aromatic group;

$R^3$ is selected from any one of the substituted groups as follows: hydrogen, alkyl group substituted by $C_1$ to $C_{10}$ acyl group or aryl group substituted by aromatic group;

R is selected from any one of the substituted groups as follows: hydrogen, straight chain or branched chain $C_1$ to $C_{10}$ alkyl group, $C_3$ to $C_8$ cycloalkyl group, straight chain or branched chain $C_2$ to $C_{10}$ alkenyl group or $C_3$ to $C_8$ cycloalkenyl group, phenyl group or phenyl group substituted by $C_1$ to $C_{10}$ alkyl group, $C_2$ to $C_6$ alkynyl group, nucleophiles containing secondary amine group including straight chain or branched chain alkyl amino group, straight chain or branched chain alkenyl amino group; aromatic or aromatic alkylamino group, the amine obtained by addition of chain alkynyl amine group and α,β-unsaturated ketones.

However, R, $R^2$, $R^3$, $R^4$ are not simultaneously hydrogen on Formula (I).

In a preferred embodiment, according to the present invention, the above-described gambogenic acid derivative is represented by the molecular structure as shown in any one of Formula (III) to (V):

Formula (III)

Formula (IV)

Formula (V)

In a preferred embodiment, according to the present invention, the above-described gambogenic acid derivative is represented by the molecular structure as shown in Formula (VI):

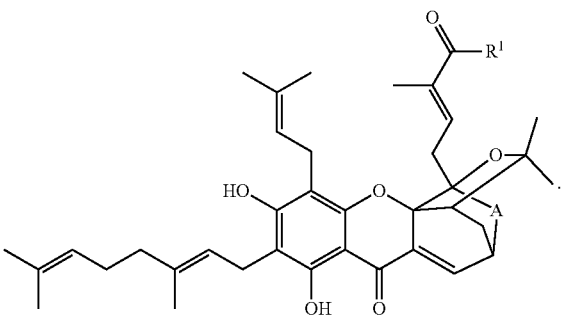

Formula (VI)

In the formula of the gambogenic acid derivative as above-described of the present invention, $R^1$ is preferably selected from any one of the following:

1) —$OR^4$, wherein $R^4$ is selected from the group consisting of any one of the following: hydrogen, methyl group, ethyl group, propyl group, isopropyl group, butyl group, isobutyl group, tert-butyl group, hexyl group, octyl group, $C_1$ to $C_{10}$ alkyl group substituted by any 1 to 3 substituted groups including oxygen group, halogen, $C_1$ to $C_{10}$ alkoxy group, acyloxy group, $C_1$ to $C_{10}$ alkoxyacyl group, aromatic group; cyclohexyl group, cyclopentyl group; cyclopropyl group, —$CH_2CH_2OCH_2CH_3$, —$CH_2CH_2OCH_2CH_2OCH_2CH_3$, —$CH_2CH_2NHCH_3$, —$OCH_2O$—, halogen, haloalkyl group, hydroxyl group, —$CH_2CH_2N(CH_2CH_3)_2$, —$CH_2CH_2OCH_2CH_2NCH_3$, benzyl group, phenethyl group, phenylpropyl group, tetrahydro-pyrrolyl group, piperidinyl group, morpholinyl group, —$CH_2CH_2OCH_2CH_2OCH_2NHCH_3$, —$CH_2CH_2NHCH_2CH_3$, —$CH_2$(N-ethylpyrrolidine), —$CH_2C(CH_3)CH_2N(CH_3)$, $C_1$ to $C_{10}$ alkyl group substituted by optionally 1 to 3 substituted aromatic groups including acyl group, aryl group, $C_3$ to $C_8$ cycloalkyl group, $C_1$ to $C_{10}$ alkyl group, hydroxyl group, acyloxy group, $C_1$ to $C_{10}$ alkoxy group; heteroarylalkyl group including $C_1$ to $C_{10}$ alkoxy group substituted by heteroaryl group, and $C_1$ to $C_{10}$ alkyl group optionally substituted by any heteroaryl group including heteroaryl group, $C_1$ to $C_{10}$ alkyl group, aralkyl group, $C_3$ to $C_8$ cycloalkyl group, $C_1$ to $C_{10}$ alkoxycarbonyl group, carbamoyl group, aromatic group and $C_1$ to $C_6$ amide group; straight chain or branched $C_2$ to $C_{10}$ alkenyl group or alkenyl group containing optionally 1 to 3 substituted groups including oxygen group, halogen, aromatic ring group, aralkyl group, $C_1$ to $C_{10}$ alkoxy group, acyloxy group, amide group, $C_1$ to $C_6$ amine acyl group, $C_1$ to $C_{10}$ alkoxy group, aryloxy group, and $C_1$ to $C_{10}$ heteroalkyl group containing 1, 2 or 3 heteroatoms; $C_4$ to $C_{10}$ cycloalkenyl, $C_4$ to $C_{10}$ alkynyl group, or $C_4$ to $C_{10}$ alkynyl group containing optionally 1 to 3 substituted groups including oxygen group, halogen, aromatic ring group, aralkyl group, $C_1$ to $C_{10}$ alkoxy group, acyloxy group, amide group, $C_1$ to $C_6$ amine acyl group, $C_1$ to $C_{10}$ alkoxy group, aryloxy group and $C_1$ to $C_{10}$ heteroalkyl group containing 1, 2 or 3 heteroatoms.

2) —NR$^5$R$^6$;

wherein R$^5$ and R$^6$ may be identical or different, and are independently selected from any one of the substituted groups as follows: hydrogen, methyl group, ethyl group, propyl group, isopropyl group, butyl group, isobutyl butyl group, tert-butyl group, hexyl group, octyl group; C$_1$ to C$_{10}$ alkyl group containing optionally 1 to 3 substituted groups including hydroxyl group, amino group, C$_1$ to C$_{10}$ alkylamino group, oxygen group, halogen, C$_1$ to C$_{10}$ alkoxy group, acyloxy group, C$_1$ to C$_{10}$ alkoxyacyl group, aryloxy group; cyclohexyl group, cyclopentyl group, cyclopropyl group, —CH$_2$CH$_2$OCH$_2$CH$_3$, —CH$_2$CH$_2$OCH$_2$CH$_2$OCH$_2$CH$_3$, —CH$_2$CH$_2$NHCH$_3$, —CH$_2$CH$_2$N(CH$_2$CH$_3$)$_2$, —CH$_2$CH$_2$OCH$_2$CH$_2$NCH$_3$, —CH$_2$(N-ethyl-pyrrolidine), tetrahydro-pyrrolyl group, piperidinyl group, morpholinyl group, benzyl group, —CH$_2$CH$_2$OCH$_2$CH$_2$OCH$_2$NHCH$_3$, —CH$_2$CH$_2$NHCH$_2$CH$_3$, phenethyl group, phenylpropyl group, —CH$_2$C(CH$_3$)CH$_2$N(CH$_3$); C$_1$ to C$_{10}$ alkyl group optionally substituted by 1 to 3 substituted aromatic groups including acyl group, —OCH$_2$O—, halogen, haloalkyl group, aryl group, C$_3$ to C$_8$ cycloalkyl group, C$_1$ to C$_{10}$ alkyl group, hydroxyl group, acyloxy group, C$_1$ to C$_{10}$ alkoxy group; heteroarylalkyl group including C$_1$ to C$_{10}$ alkoxy group substituted by heteroaryl group, and C$_1$ to C$_{10}$ alkyl group optionally substituted by any heteroaryl group including heteroaryl group, C$_1$ to C$_{10}$ alkyl group, aralkyl group, C$_3$ to C$_8$ cycloalkyl group, C$_1$ to C$_{10}$ alkoxycarbonyl group, carbamoyl group, aromatic group and C$_1$ to C$_6$ amide acyl group; straight chain or branched chain C$_1$ to C$_{10}$ alkenyl group or alkynyl group containing optionally 1 to 3 substituted groups including oxygen group, halogen, aromatic ring group, aralkyl group, C$_1$ to C$_{10}$ alkoxy group, acyloxy group, amide group, C$_1$ to C$_6$ amine acyl group, C$_1$ to C$_{10}$ alkoxy group, aryloxy group and C$_1$ to C$_{10}$ heteroalkyl group containing 1, 2 or 3 heteroatoms; C$_4$ to C$_{10}$ cycloalkenyl, C$_4$ to C$_{10}$ alkynyl group, or C$_4$ to C$_{10}$ alkynyl group containing optionally 1 to 3 substituted groups including oxygen group, halogen, aromatic ring group, aralkyl group, C$_1$ to C$_{10}$ alkoxy group, acyloxy group, amide group, C$_1$ to C$_6$ amine acyl group, C$_1$ to C$_{10}$ alkoxy group, acyloxy group, and C$_1$ to C$_{10}$ heteroalkyl group containing 1, 2 or 3 heteroatoms.

R$^3$ is selected from any one of the substituted groups as follows: hydrogen, formyl group, acetyl group, carbamoyl group, phenyl group, and phenylacetyl group.

R$^2$ is selected from any one of the substituted groups as follows: hydrogen, methyl group, ethyl group, propyl group, isopropyl group, butyl group, isobutyl group, tert-butyl group, hexyl group, octyl group, cyclopropyl group, cyclobutyl group, cyclopentyl group, cyclohexyl group, cycloheptyl group, benzyl group, phenethyl group, furyl group, pyranyl group, 2H-pyrrolyl group, pyrrolyl group, imidazolyl group, pyrazolyl group, pyridyl group, formyl group, acetyl group, carbamoyl acyl group, phenyl group, and phenylacetyl group.

R is selected from any one of the substituted groups as follows: methyl group, ethyl group, propyl group, isopropyl group, butyl group, isobutyl group, tert-butyl group, hexyl group, octyl group, cyclohexyl group, cyclopentyl group, vinyl group, butene group, hexenyl group, cyclohexenyl group, cyclopentenyl group, phenyl group, benzyl group, phenethyl group, phenylpropyl group, butynyl group, hexynyl group, morpholinyl group, piperidinyl group, and piperazinyl group.

In a preferred embodiment, according to the present invention, in the formula of the above-described gambogenic acid derivative:

A is —CO— or —HC(OH)—

R$^1$ is selected from:

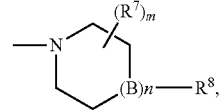

1)

wherein R$^7$ is selected from the group consisting of any one of the following: substituted group as defined in R$^5$, carbonyl group, alkylene group, oxime group;

m, n is 0, 1, 2 or 3;

B is carbon, nitrogen or oxygen;

the group of R$^8$ is identical as the group defined in R$^5$, or R$^8$ is oxygen so as to form nitrogen oxides with B.

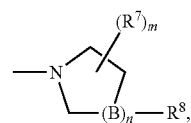

2)

wherein R$^7$ is selected from the group consisting of any one of the following:

the substituted group as in defined R$^5$, carbonyl group, imino group, aliphatic group;

m, n is 0, 1, 2 or 3;

B is carbon, nitrogen or oxygen;

the group of R$^8$ is identical with the group as defined in R$^5$, or R$^8$ is oxygen so as to form nitrogen oxides with B.

In a second aspect, the present invention is to provide a salt of the gambogenic acid derivatives, the salt can be 1) the salt formed with inorganic acid such as hydrochloric acid salts, carbonates, sulfates; 2) the salt formed with an organic base; or 3) the salt formed with an inorganic base; 4) the salt formed with organic acid.

In a third aspect, the present invention is to provide a method for preparing gambogenic acid derivative, gambogenic acid derivative as shown in Formula (VII) is obtained by R$^2$ and R$^3$ introduced to the gambogenic acid or gambogenic acid derivative of Formula (VI), wherein the order of R$^2$ and R$^3$ introduction may be adjusted;

wherein R$^3$ is condensed with R$^3$X acid halide or acid anhydride (R$^3$)$_2$O; X is Cl, Br or I;

When R$^2$ is acyl group substituted by alkyl group, acyl group substituted by aromatic group, introduced in the same method with the introduction of R$^3$; when R$^2$ is alkyl group, cycloalkyl group or heteroaryl group, the introduction is via etherification reaction by halo of R$^2$.

Then, the carbonyl group of C$_6$ carbon was prepared by reduction to obtain gambogenic acid derivatives as shown in Formula (VIII), and/or by esterification or acidification with R$^4$OH, R$^5$R$^6$NH or

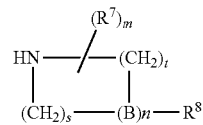

to obtain gambogenic acid derivatives as shown in Formula (III).

The reaction solvent of condensation of $R^2$ and/or $R^3$ can be methyl chloride (such as dichloromethane, chloroform), chlorinated ethane, tetrahydrofuran, etc. The reaction temperature is preferably between 20° C. to 40° C. The deacid reagent (such as triethylamine, pyridine) or catalyst (such as DMAP) can be added accordingly. When $R^2$ and $R^3$ are different, the molar ratio of acid halide or acid anhydride and gambogenic acid is 5:1.

Halide of $R^2$ can be $R^2Br$, $R^2I$. Preferably, the reaction condition contains the sodium carbonate, potassium carbonate, cesium carbonate or bicarbonate. Preferably, the reaction solvent is a polar solvent such as DMA or DMF.

The reducing agents used for reduction reaction on $C_6$ include such as sodium borohydride, lithium borohydride, useful solvents including $C_1$ to $C_6$ alcohol and tetrahydrofuran.

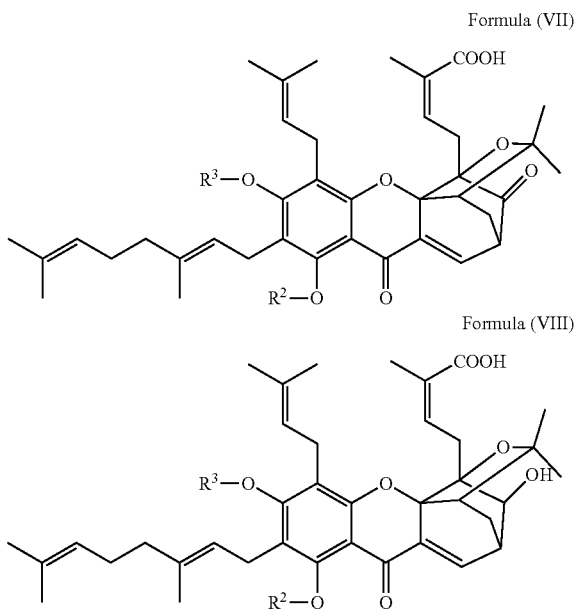

In a fourth aspect, the present invention is to provide a second method for preparing gambogenic acid derivative, wherein gambogenic acid, gambogenic acid derivatives as shown in Formula (VII), or gambogenic acid derivatives as shown in Formula (VIII) are used as raw material; the double bond is oxidized between $C_9$ and $C_{10}$ to obtain gambogenic acid derivatives as shown in Formula (II) by peroxidant in alkaline conditions.

Preferably, the concentration of hydrogen peroxide is 30%. The reaction solvent is preferably water, the base is a water-soluble hydroxide such as NaOH, KOH, etc.

In a fifth aspect, the present invention is to provide a third preparation method of gambogenic acid derivative, wherein gambogenic acid derivative as shown in Formula (I) was prepared by 1,4-addition on double bond between $C_9$ and $C_{10}$ by the organic copper reagent RCu with gambogenic acid, gambogenic acid derivative as shown in Formula (VII), or gambogenic acid derivative as shown in Formula (VIIII).

Preferably, the reaction solvent of addition is tetrahydrofuran, carbon dichloride, etc. The reaction temperature is preferably from −10° C. to −50° C., more preferably is −20° C.

Another aspect of the present invention is to provide a use for antitumor drug of said gambogenic acid derivative. The gambogenic acid anticancer drugs can be an injection, powder and other formulations.

The tumors include, but are not limited to, human skin cancer, human thyroid cancer, human breast cancer, human gastric cancer, human colorectal cancer, human liver cancer, human lung cancer, human ovarian cancer, human head and neck cancer, human kidney cancer, human bladder cancer, human sarcoma (bone, cartilage, striated muscle, etc.), human malignant lymphoma, human leukemia, human prostate cancer, human malignant glioma, human cervical cancer, human esophageal cancer, human testicular cancer, human malignant teratoma.

The gambogenic acid derivative of the present invention has better antitumor activity, better security and simplified preparation by experimental verification.

DETAIL DESCRIPTION OF THE INVENTION

The present invention provides a gambogenic acid derivative, a salt of gambogenic acid derivative, and the preparation method and use of said gambogenic acid derivative.

Figure 1:
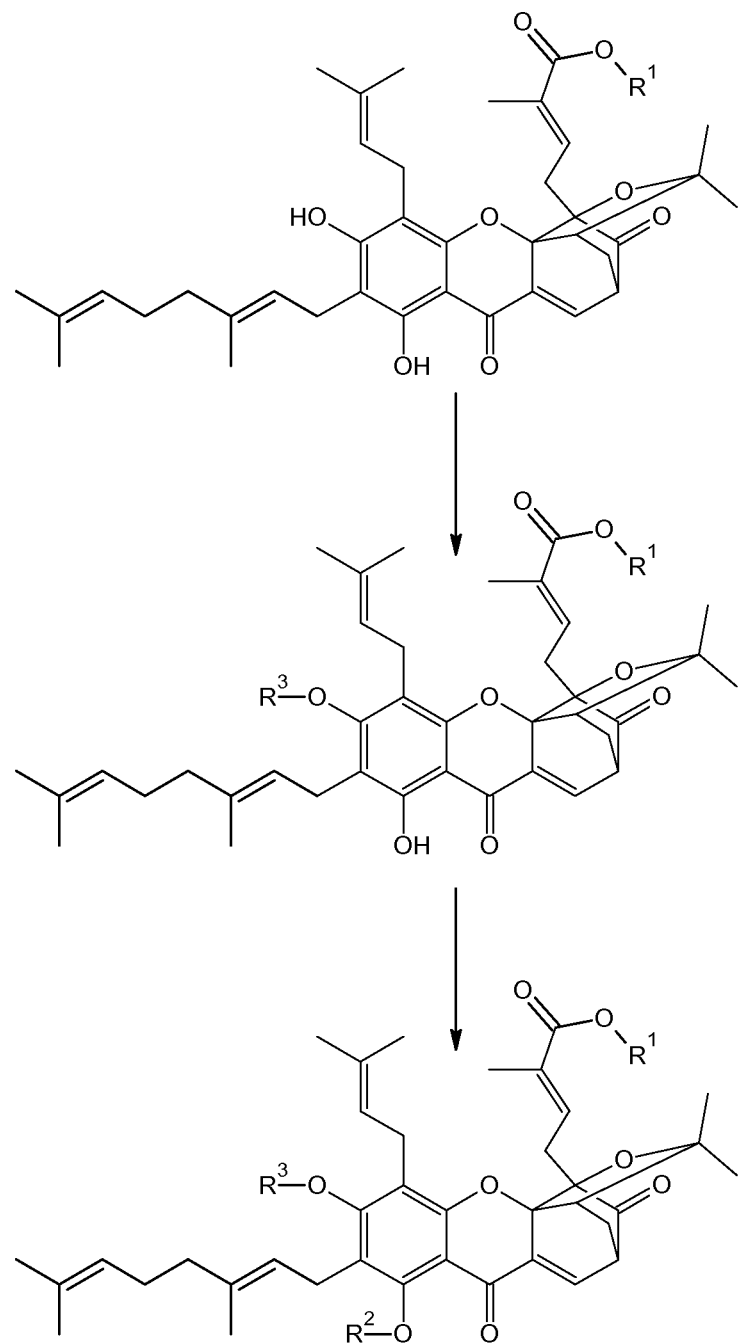
FIG. 1 is a flow chart of a first method for gambogenic acid derivative in accordance with the present invention.

The structure of the gambogenic acid derivative of the present invention is as shown in Formula (I) and/or (II), and is preferably any one of Formula (III) to (VI). The first embodiment of gambogenic acid derivative preparation of the present invention as shown in FIG. 1, the raw materials is gambogenic acid, $R_2$ and $R_3$ introduced, wherein the order of the introduction of $R_2$ and $R_3$ can be adjusted.

Figure 2:
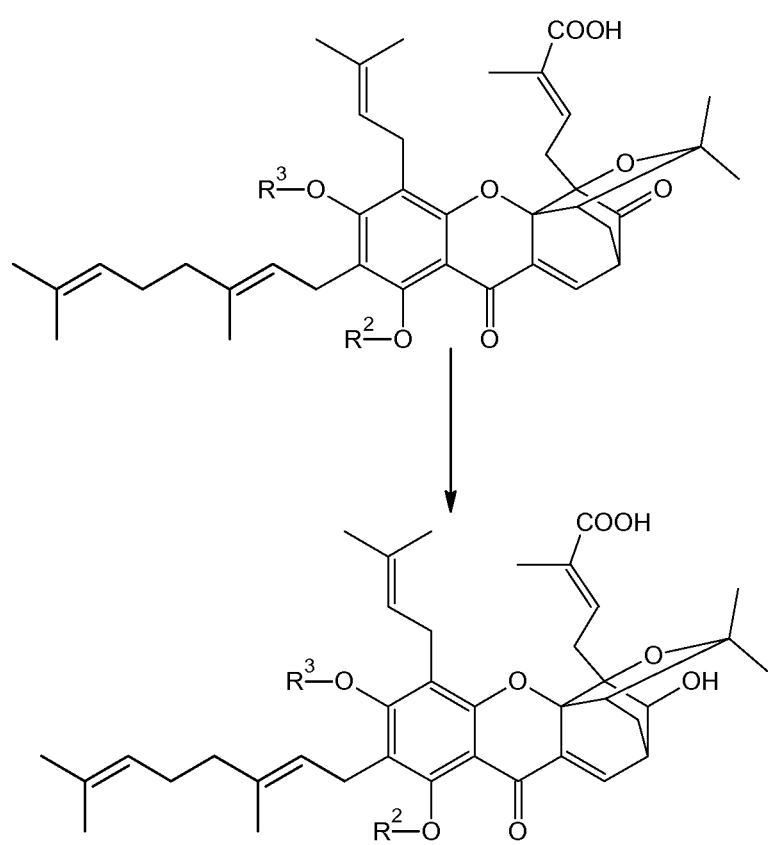
FIG. 2 is a flow chart of a second method for gambogenic acid derivative in accordance with the present invention.

The second embodiment of gambogenic acid derivative preparation of the present invention as shown in FIG. 2, the raw materials are gambogenic acid or the gambogenic acid derivative prepared from the first embodiment, and carbonyl group of $C_6$ carbon is reduced to a hydroxyl group.

Figure 3:
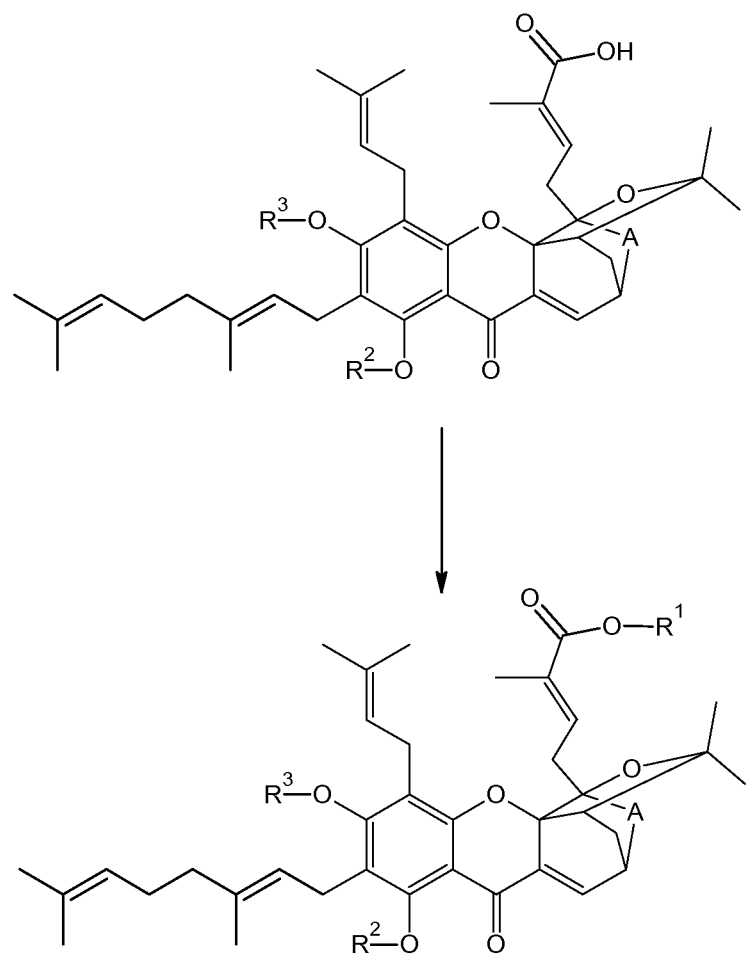
FIG. 3 is a flow chart of a third embodiment for gambogenic acid derivative in accordance with the present invention.

The third embodiment for gambogenic acid derivatives preparation of the present invention as shown in FIG. 3, the raw materials is gambogenic acid or the gambogenic acid derivative prepared from the first embodiment or the second embodiment, and then the gambogenic acid derivative obtained by esterification with $R^4OH$, or by acidification with $R^5R^6NH$ or

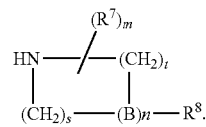

Figure 4:
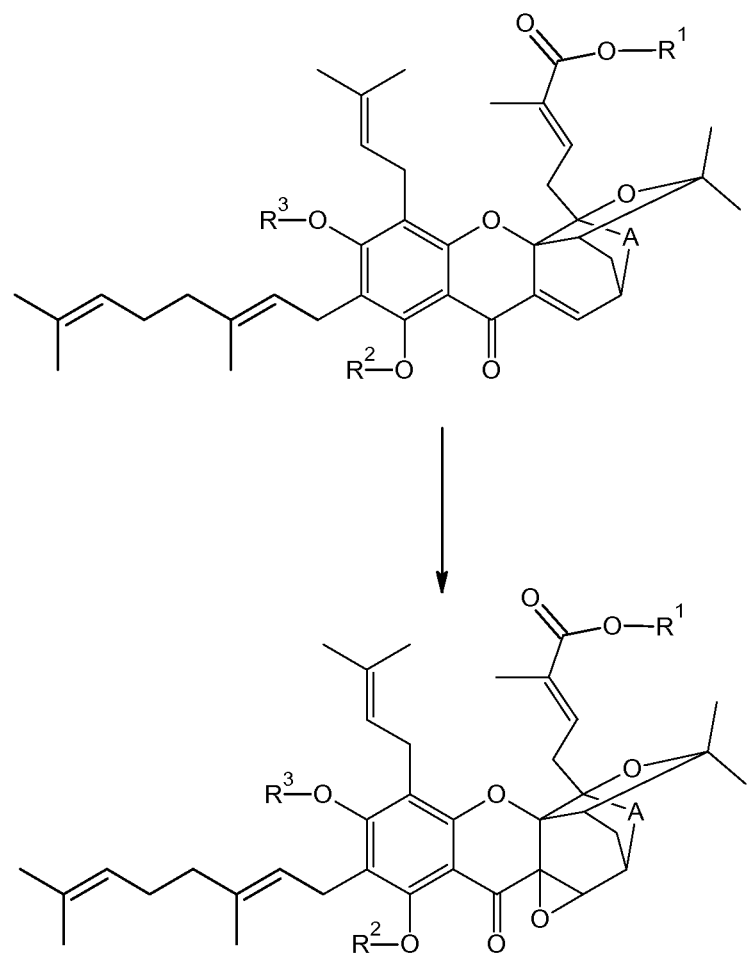
FIG. 4 is a flow chart of a fourth embodiment for gambogenic acid derivative in accordance with the present invention.

The fourth embodiment for gambogenic acid derivatives preparation of the present invention as shown in FIG. 4, the raw material is gambogenic acid, or the gambogenic acid derivative as shown in Formula (VII), or the gambogenic acid derivative as shown in Formula (VIII), and the double bond between $C_8$ and $C_9$ was oxidized to prepare gambogenic acid derivative.

Figure 5:
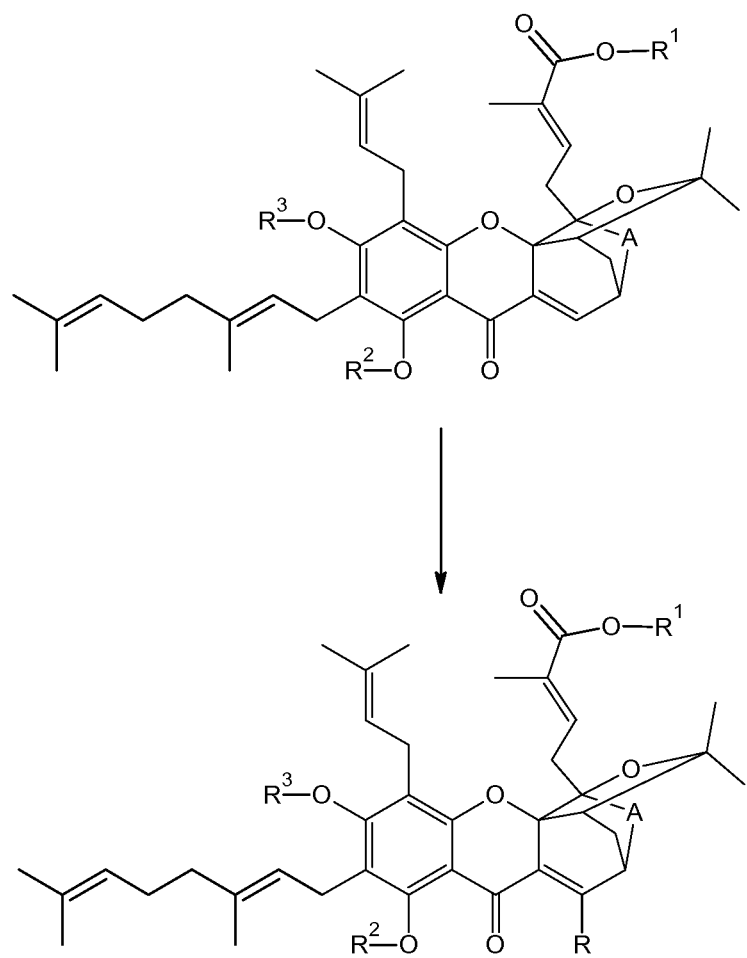
FIG. 5 is a flow chart of a fifth embodiment for gambogenic acid derivative in accordance with the present invention.

The fifth embodiment for gambogenic acid derivatives preparation of the present invention as shown in FIG. 5, the raw material is gambogenic acid, or the gambogenic acid derivative as shown in Formula (VII), or the gambogenic acid derivative as shown in Formula (VIII), and the gambogenic acid derivative obtained by addition on double bond between the $C_9$ and $C_{10}$ by the organic copper reagent RCu.

As shown in FIG. 1 to FIG. 5 and Formula (I) to (VIII):

A is —CO— or —HC(OH)—; $R^1$ is selected from:

1) —$OR^4$;

wherein $R^4$ is selected from the group consisting of any one of the following: hydrogen, straight chain or branched chain $C_1$ to $C_{10}$ alkyl group, or alkyl group containing optionally 1 to 3 substituted group including oxygen group, halogen, $C_1$ to $C_{10}$ alkoxy group, acyloxy group, $C_1$ to $C_{10}$ alkoxycarbonyl group, aryloxy group; $C_3$-$C_8$ cycloalkyl group, $C_1$ to $C_{10}$ alkyl group substituted by 1, 2 or 3 heteroatoms; alkylaryl group includes $C_1$ to $C_{10}$ alkyl group substituted by aromatic group and $C_1$ to $C_{10}$ alkyl group optionally substituted by 1 to 3 substituted aromatic group including acyl group, —$OCH_2O$—, halogen, haloalkyl group, aryl group, $C_3$ to $C_8$ cycloalkyl group, $C_1$ to $C_{10}$ alkyl group, hydroxyl group, acyloxy group, $C_1$ to $C_{10}$ alkoxy group; heteroarylalkyl group includes $C_1$ to $C_{10}$ alkoxy group substituted by heteroaryl group, and $C_1$ to $C_{10}$ alkyl group optionally substituted by any heteroaryl group including heteroaryl group, $C_1$ to $C_{10}$ alkyl group, aralkyl group, $C_3$ to $C_8$ cycloalkyl group, $C_1$ to $C_{10}$ alkoxycarbonyl group, carbamoyl group, aromatic group and $C_1$ to $C_6$ amide group; straight chain or branched chain $C_2$ to $C_{10}$ alkenyl group or alkynyl group including optionally 1 to 3 substituted groups including oxygen group, halogen, aromatic ring group, aralkyl group, $C_1$ to $C_{10}$ alkoxy group, acyloxy group, amide group, $C_1$ to $C_6$ amine acyl group, $C_1$ to $C_{10}$ alkoxy group and $C_1$ to $C_{10}$ heteroalkyl group including 1, 2 or 3 heteroatoms; $C_4$ to $C_{10}$ cycloalkenyl, $C_4$ to $C_{10}$ alkynyl group, or alkynyl group including optionally 1 to 3 substituted groups including oxygen group, halogen, aromatic ring group, aralkyl group, $C_1$ to $C_{10}$ alkoxy group, acyloxy group, amide group, $C_1$ to $C_6$ acyl group, $C_1$ to $C_{10}$ alkoxy group, aryloxy group and $C_1$ to $C_{10}$ heteroalkyl group including optionally 1, 2 or 3 heteroatoms.

2) —$NR^5R^6$;

wherein $R^5$ and $R^6$ may be identical or different, and are independently selected from any one of the substituted groups as follows: hydrogen; straight chain or branched $C_1$ to $C_{10}$ alkyl group or $C_1$ to $C_{10}$ alkyl group containing optionally 1 to 3 substituted group including oxygen group, halogen, $C_1$ to $C_{10}$ alkoxy group, acyloxy group, $C_1$ to $C_{10}$ alkoxyacyl group, aryloxy group; $C_3$ to $C_8$ cycloalkyl group; $C_1$ to $C_{10}$ alkyl group substituted by 1, 2 or 3 heteroatoms; alkylaryl group including $C_1$ to $C_{10}$ alkyl group substituted by aromatic group and $C_1$ to $C_{10}$ alkyl group substituted by optionally 1 to 3 substituted aromatic groups including acyl group, —$OCH_2O$—, halogen, haloalkyl group, hydroxyl group, aryl group, $C_3$ to $C_8$ cycloalkyl group, $C_1$ to $C_{10}$ alkyl group, acyloxy group, $C_1$ to $C_{10}$ alkoxy group; heteroarylalkyl group including $C_1$ to $C_{10}$ alkoxy group substituted by heteroaryl group, and $C_1$ to $C_{10}$ alkyl group optionally substituted by any heteroaryl group including heteroaryl group, $C_1$ to $C_{10}$ alkyl group, aralkyl group, $C_3$ to $C_8$ cycloalkyl group, $C_1$ to $C_{10}$ alkoxycarbonyl group, carbamoyl group, aromatic group and $C_1$ to $C_6$ amide group; straight chain or branched chain $C_2$ to $C_{10}$ alkenyl group or alkenyl group containing optionally 1 to 3 substituted groups including oxygen group, halogen, aromatic ring group, aralkyl group, $C_1$ to $C_{10}$ alkoxy group, acyloxy group, amide group, $C_1$ to $C_6$ amine acyl group, $C_1$ to $C_{10}$ alkoxy group, aryloxy group and $C_1$ to $C_{10}$ heteroalkyl group containing 1, 2 or 3 heteroatoms; $C_4$ to $C_{10}$ cycloalkenyl, $C_4$ to $C_{10}$ alkynyl group, or alkynyl group containing optionally 1 to 3 substituted groups including oxygen group, halogen, aromatic ring group, aralkyl group, $C_1$ to $C_{10}$ alkoxy group, acyloxy group, amide group, $C_1$ to $C_6$ acyl group, $C_1$ to $C_{10}$ alkoxy group, aryloxy group and $C_1$ to $C_{10}$ heteroalkyl group including 1, 2 or 3 heteroatoms.

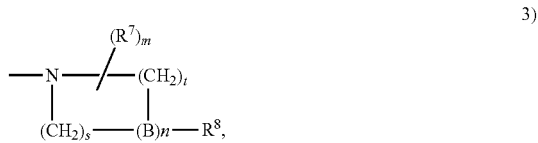

3)

wherein s and t are positive integers, and the sum of s and t is a natural number of 2 to 10;

m is 0, 1, 2 or 3, represents the number of the substituted group on $R^7$ of the ring;

n is 0, 1, 2 or 3, represents the number of B on the ring; B is carbon, nitrogen or oxygen;

the groups of $R^7$, $R^8$ are identical with the group of $R^5$, or carbonyl group, imino group, oxime group, aliphatic group; or when B is tertiary nitrogen, $R^8$ is oxygen, and so as to form nitrogen oxides with B;

$R^2$ is selected from any one of the substituted groups as follows: hydrogen, straight chain or branched chain $C_1$ to $C_{10}$ alkyl group, $C_3$ to $C_8$ cycloalkyl group, aromatic group or aromatic group substituted by $C_1$ to $C_{10}$ alkyl, heteroaryl group, acyl group substituted by $C_1$ to $C_{10}$ alkyl or acyl group substituted by aromatic group;

$R^3$ is selected from any one of the substituted groups as follows: hydrogen, $C_1$ to $C_{10}$ acyl group substituted by alkyl group or aryl group substituted by aromatic group;

R is selected from any one of the substituted groups as follows: hydrogen, straight chain or branched chain $C_1$ to $C_{10}$ alkyl group, $C_3$ to $C_8$ cycloalkyl group, straight chain or branched chain $C_2$ to $C_{10}$ alkenyl group or $C_3$ to $C_8$ cycloalkenyl group, phenyl group or phenyl group substituted by $C_1$ to $C_{10}$ alkyl group, $C_2$ to $C_6$ alkynyl group, nucleophiles containing secondary amine group including straight chain or branched chain alkyl amino group, straight chain or branched chain alkenyl amino group; aromatic or aromatic alkylamino group, the amine obtained by addition of chain alkynyl amine group and α,β-unsaturated ketones.

However, R, $R^1$, $R^2$, $R^3$ are not simultaneously hydrogen on the Formula (I).

Other objectives, advantages and novel features of the invention will become more apparent from the following detailed description when taken in conjunction with the accompanying drawings.

Example 1

Preparation of methyl gambogenic acid $R^1$ is a methyl group in Formula (VI).

With reference to FIG. 3, 20 mg gambogenic acid, 6.5 mg sodium hydrogencarbonate, 1 ml DMA (N,N-dimethylacetamide), 15 μl iodomethane were added into a 10 ml reaction flask and in the dark at room temperature.

Progress of the reaction was monitored by thin layer chromatography (TLC). After completion of the reaction, the reaction solution was poured into 50 ml water, extracted with ether, washed with saline, dried by anhydrous sodium sulfate, and chromatographed (eluent is ethyl acetate/petroleum ether, the volume ratio is 1:12) to obtain 9 mg orange-yellow jelly.

Example 2

Preparation of 6-methoxy methyl ester gambogenic acid $R^1$ is methyl group, $R^2$ is methyl group, and $R^3$ is H in the Formula (III).

With reference to FIG. 1, 20 mg methyl gambogenic acid obtained from the example 1, 12 mg potassium, 1 ml DMA, 15 μl iodomethane were added into a 25 ml reaction flask and in the dark at room temperature.

After completion of the reaction, the reaction solution was poured into 50 ml water, and extracted with ether, washed with water, dried and chromatographed (eluent is ethyl acetate/petroleum ether, the volume ratio is 1:12) to obtain 12 mg orange-yellow jelly.

Example 3

Preparation of ethyl ester gambogenic acid $R^1$ is an ethyl group in Formula (VI).

With reference to FIG. 3, 20 mg gambogenic acid, 6.5 mg sodium bicarbonate, 1 ml DMA, and 15 μl bromoethane were added into a 10 ml reaction flask and in the dark at room temperature.

After completion of the reaction, the reaction solution was poured into 50 ml water conductivity, extracted with ether, chromatographed (eluent is ethyl acetate/petroleum ether, the volume ratio is 1:12) to obtain 9 mg orange-yellow jelly.

Example 4

Preparation of 6-ethoxyl gambogenic acid ethyl ester $R^1$ is ethyl group, $R^2$ is ethyl group, $R^3$ is H in Formula (III).

With reference to FIG. 1, 20 mg methyl gambogenic acid obtained from the example 1, 6 mg potassium carbonate, 1 ml DMA (N,N-dimethylacetamide), 15 μl bromoethane were added into a 25 ml reaction flask and in the dark at room temperature.

After completion of the reaction, the reaction solution was poured into 50 ml water, extracted with ether, washed with water, dried and chromatographed (eluent is ethyl acetate/petroleum ether) (the volume ratio is 1:12) to obtain 9 mg orange-yellow jelly.

Example 5

Preparation of piperidine gambogenic acid $R^1$ is

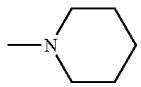

in Formula (VI).

With reference to FIG. 3, 15.6 mg gambogenic acid and 0.5 ml dichloromethane were ice-bath cooled to 0° C. to form an ice-solution in a 10 ml reaction flask. 6 mg 1-(3-dimethylaminopropyl)-3-ethylcarbodiimide carbodiimide hydrochloride (EDCI), 3.6 mg 1-hydroxybenzotriazole triazole (HOBT), 4.8 μl anhydrous piperidine and 0.4 ml dichloromethane were dubbed into the ice-solution.

The ice-solution was warmed naturally to room temperature and stirred to obtain a reaction solution. After completion of the reaction, the reaction solution was diluted with 50 ml dichloromethane, washed with 0.5 M aqueous sulfuric acid solution, saturated saline, dried over anhydrous sodium sulfate and then the solvent was evaporated, chromatographed (eluent is ethyl acetate/petroleum ether/diethyl chloromethane) (the volume ratio is 1:4:1), and then eluted to obtain 5 mg yellow jelly.

Example 6

Preparation of diethylamide gambogenic acyl $R^1$ is —N(CH$_3$2 CH$_3$)$_2$.

With reference to FIG. 3, 20 mg gambogenic acid and 0.5 ml dichloromethane were ice-bath cooled to 0° C. to form an ice-solution in a 10 ml reaction flask. 6 mg EDCI, 3.6 mg HOBT, 10 μl ethylenediamine and 0.5 ml dichloromethane were dubbed into the ice-solution.

The ice-solution was warmed naturally to room temperature and stirred to obtain a reaction solution. After completion of the reaction, the reaction solution was diluted with 50 ml dichloromethane, washed with 0.5 M aqueous sulfuric acid solution, saturated saline, dried with anhydrous sodium sulfate and then the solvent was evaporated, chromatographed (eluent is ethyl acetate/petroleum ether/diethyl chloromethane) (the volume ratio is 1:4:1), and then eluted to obtain 7 mg yellow jelly.

Example 7

Preparation of morpholine gambogenic acid $R^1$ is

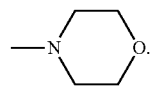

With reference to FIG. 3, 15.6 mg gambogenic acid and 0.5 ml dichloromethane were ice-bath cooled to 0° C. to form an ice-solution in a 10 ml reaction flask. 10 mg EDCI, 6 mg HOBT, 5 μl morpholine and 0.4 ml dichloromethane were dubbed into the ice-solution.

The ice-solution was warmed naturally to room temperature and stirred to obtain a reaction solution. 3 mg HOBT, 5 μl morpholine were added to the reaction solution additionally. After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed (eluent is chloroform/ethyl acetate) (the volume ratio is 8:1), and then eluted to obtain 5 mg orange-yellow jelly.

Example 8

Preparation of 12-hydroxy gambogenic acid

The Formula of 12-hydroxy gambogenic acid is as follows:

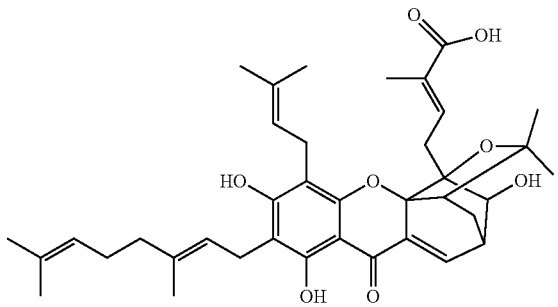 [SMILES: CC(C)=CCC/C(C)=C/Cc1c(O)c(CC=C(C)C)c2c(c1O)C(=O)C1=CC3CC4C(C)(C)OC(C/C=C(\C)C(=O)O)(CC3O)C14O2]

With reference to FIG. 2, 20 mg gambogenic acid and 4 ml methanol were ice-bath cooled to −5° C. to form an ice-solution in a 10 ml reaction flask. The ice-solution was added 44 mg sodium borohydride to form a mixture. The mixture was dried for 1 h, and then warmed naturally to room temperature for 3 hours to complete reaction.

3 M hydrochloric acid aqueous solution was added to quench the reaction to form a reaction solution. The reaction solution was diluted with 50 ml ethyl acetate, and then washed with 0.5 M hydrochloric acid aqueous solution, saturated saline, and then dried with anhydrous sodium sulfate, and then the solvent was evaporated, chromatographed (eluent is ethyl acetate acetate/dichloromethane) (the volume ratio is 1:4), and then eluted to obtain 9 mg orange-yellow jelly.

Example 9

Preparation of 8,9-epoxy gambogenic acid

The Formula of 8,9-epoxy gambogenic acid structure is as follows:

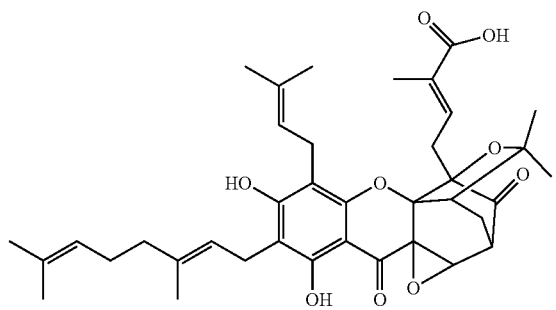 [SMILES: CC(C)=CCC/C(C)=C/Cc1c(O)c(CC=C(C)C)c2c(c1O)C(=O)C13OC1C1CC4C(C)(C)OC(C/C=C(\C)C(=O)O)(CC1=O)C43O2]

With reference to FIG. 4, 50 mg gambogenic acid, 0.5 ml and 2M sodium hydroxide aqueous solution, and 0.2 ml hydrogen peroxide were added into a 10 ml reaction flask and reacted at room temperature to form a reaction solution.

After completion of the reaction, the reaction solution was extracted by ethyl acetate, and washed with 1.0 M hydrochloric acid aqueous solution, saturated saline, and dried with anhydrous sodium sulfate, and then the solvent was evaporated, chromatographed (eluent is ethyl acetate/petroleum ether) (the volume ration is 1:3), and then eluted to obtain 12 mg orange-yellow jelly.

Example 10

Preparation of gambogenic acyl n-butylamine

A is —CO—, $R^1$ is —NH—$(CH_2)_{10}$—$CH_3$, in the Formula (VI).

20 mg gambogenic acid and 0.5 ml dichloromethane were ice-bath cooled to 0° C. to form an ice-solution in a 10 ml reaction flask. 10 mg EDCI, 4.5 mg HOBT, 6 μl n-butylamine and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed by silicagel column (eluent is ethyl acetate/petroleum ether/dichloromethane) (the volume ratio is 1:8:1), and then eluted to obtain 7 mg orange-yellow jelly.

Example 11

Preparation of gambogenic acyl undecylamine

A is —CO—, $R^1$ is —NH—$(CH_2)_{10}$—$CH_3$, in Formula (VI).

20 mg gambogenic acid and 0.5 ml dichloromethane were ice-bath cooled to 0° C. to form an ice-solution in a 10 ml reaction flask. 10 mg EDCI, 4.5 mg HOBT, 6 μl n-undecylamine and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed by silicagel column (eluent is ethyl acetate/petroleum ether/dichloromethane (the volume ratio is 1:8:1), and then eluted to obtain 7 mg orange-yellow jelly.

Example 12

Preparation of gambogenic acyl isopropylamine

A is —CO—, $R^1$ is —NH—$CH(CH_3)_2$, in Formula (VI).

20 mg gambogenic acid and 0.5 ml dichloromethane were ice-bath cooled to 0° C. to form an ice-solution in a 10 ml reaction flask. 10 mg EDCI, 4.5 mg HOBT, 5 μl isopropylamine and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed by silicagel column (eluent is ethyl acetate/petroleum ether/dichloromethane) (the volume ratio is 1:8:1), and then eluted to obtain 7 mg orange-yellow jelly.

Example 13

Preparation of gambogenic acyl dipropylamine

A is —CO—, $R^1$ is —$NHR^5R^6$, wherein $R^5$ and $R^6$ are both propyl group in the Formula (VI).

20 mg gambogenic acid and 0.5 ml dichloromethane were ice-bath cooled to 0° C. to form an ice-solution in a 10 ml reaction flask. 10 mg EDCI, 4.5 mg HOBT, 8 μl dipropylamine and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed by silicagel column (eluent is ethyl acetate/petroleum ether/dichloromethane (the volume ratio is 1:4:1), and then eluted to obtain 7 mg orange-yellow jelly.

Example 14

Preparation of gambogenic acyl isobutylamine

A is —CO—, $R^1$ is —NH—$C(CH_3)$—$CH_2$—$CH_3$ in Formula (VI).

20 mg gambogenic acid and 0.5 ml dichloromethane were ice-bath cooled to 0° C. to form an ice-solution in a 10 ml reaction flask. 10 mg EDCI, 4.5 mg HOBT, 6 μl isobutylamine and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed by silicagel column (eluent is ethyl acetate/petroleum ether/dichloromethane (the volume ratio is 1:8:1), and then eluted to obtain 7 mg orange-yellow jelly.

Example 15

Preparation of gambogenic acyl(2,6-dimethylpiperidine)

$R^1$ is

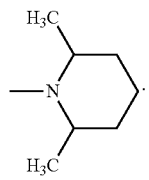

With reference to FIG. 3, 20 mg gambogenic acid and 0.5 ml dichloromethane were ice-bath cooled to 0° C. to form an ice-solution in a 10 ml reaction flask. 10 mg EDCI, 4.5 mg HOBT, 8 μl 2,6-dimethylpiperidine and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated by saline three times, dried with anhydrous sodium sulfate, and then the solvent was evaporated, chromatographed (eluent is ethyl acetate/benzene) (the volume ratio is 1:8), and then eluted to obtain 5 mg orange-yellow jelly.

Example 16

Preparation of gambogenic acyl pyrrolidine $R^1$ is

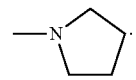

With reference to FIG. 3, 20 mg gambogenic acid and 0.5 ml dichloromethane were ice-bath cooled to 0° C. to form an ice-solution in a 10 ml reaction flask. 10 mg EDCI, 4.5 mg HOBT, 5 μl pyrrolidine and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated by saline three times, dried with anhydrous sodium sulfate, and then the solvent was evaporated, chromatographed (eluent is ethyl acetate/petroleum ether) (the volume ratio is 1:4), and then eluted to obtain 6 mg orange-yellow jelly.

Example 17

Preparation of gambogenic acid cyclohexylamine $R^1$ is

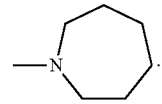

pyrrolidine FIG. 3, 20 mg gambogenic acid and 0.5 ml dichloromethane were ice-bath cooled to 0° C. to form an ice-solution in a 10 ml reaction flask. 10 mg EDCI, 4.5 mg HOBT, 7 μl cyclohexylamine and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed (eluent is ethyl acetate/petroleum ether/dichloromethane) (the volume ratio is 1:4:1), and then eluted to obtain 7 mg orange-yellow jelly.

Example 18

Preparation of gambogenic acyl(ethoxyethylamine)

$R^1$ is —NH—$(CH_2)_2$—O—$CH_2$—$CH_3$.

20 mg gambogenic acid and 0.5 ml dichloromethane were ice-bath cooled to 0° C. to form an ice-solution in a 10 ml reaction flask. 10 mg EDCI, 4.5 mg HOBT, 5 mg ethoxyethylamine and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed (eluent is ethyl acetate/petroleum ether/dichloromethane) (the volume ratio is 1:4:1), and then eluted to obtain 5 mg orange-yellow jelly.

Example 19

Preparation of gambogenic acid benzylamine $R^1$ is

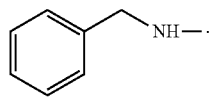

20 mg gambogenic acid and 0.5 ml dichloromethane were ice-bath cooled to 0° C. to form an ice-solution in a 10 ml reaction flask. 10 mg EDCI, 4.5 mg HOBT, 7 µl benzylamine and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed (eluent is ethyl acetate/petroleum ether/dichloromethane) (the volume ratio is 1:4:1), and then eluted to obtain 7 mg orange-yellow jelly.

Example 20

Preparation of gambogenic acyl ethoxycarbonyl methylamine $R^1$ is —NH—$CH_2$—CO—O—$CH_2$—$CH_3$.

20 mg gambogenic acid and 0.5 ml dichloromethane were ice-bath cooled to 0° C. to form an ice-solution in a 10 ml reaction flask. 10 mg EDCI, 4.5 mg HOBT, 10 mg glycine ethyl ester and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed (eluent is ethyl acetate/petroleum ether/dichloromethane) (the volume ratio is 1:4:1), and then eluted to obtain 7 mg orange-yellow jelly.

Example 21

Preparation of gambogenic acyl piperazine $R^1$ is

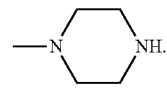

20 mg gambogenic acid and 0.5 ml dichloromethane were ice-bath cooled to 0° C. to form an ice-solution in a 10 ml reaction flask. 10 mg EDCI, 4.5 mg HOBT, 4 mg piperazine and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed (eluent is ethyl acetate/methanol) (the volume ratio is 10:1), and then eluted to obtain 7 mg orange-yellow jelly.

Example 22

Preparation of gambogenic acyl methylpiperazine and citric acid salt Thereof $R^1$ is

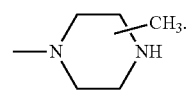

20 mg gambogenic acid and 0.5 ml dichloromethane were ice-bath cooled to 0° C. to form an ice-solution in a 10 ml reaction flask. 10 mg EDCI, 4.5 mg HOBT, 7 µl methylpiperazine and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed (eluent is ethyl acetate/petroleum ether/dichloromethane) (the volume ratio is 1:4:1), and then eluted to obtain 7 mg orange-yellow jelly.

Gambogenic acyl methylpiperazine was dissolved in ethanol, ethanol the solution having citric acid was added dropwise, the resulting precipitate was dissolved by heating, cooling pale yellow precipitate, filtered, dried to obtain gambogenic acyl methylpiperazine and citric acid salt thereof.

Example 23

Preparation of gambogenic acyl benzylpiperazine and citric acid salt Thereof $R^1$ is

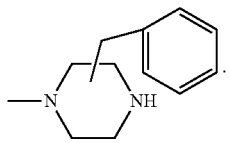

20 mg gambogenic acid and 0.5 ml dichloromethane were ice-bath cooled to 0° C. to form an ice-solution in a 10 ml reaction flask. 10 mg EDCI, 4.5 mg HOBT, 11 µl benzylpiperazine and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed (eluent is ethyl acetate/petroleum ether/dichloromethane) (the volume ratio is 1:4:1), and then eluted to obtain 7 mg orange-yellow jelly.

Example 24

Preparation of gambogenic acyl(4-acetylpiperazinyl)

$R^1$ is

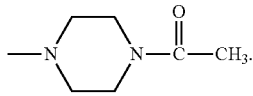

20 mg gambogenic acid and 0.5 ml dichloromethane were ice-bath cooled to 0° C. to form an ice-solution in a 10 ml reaction flask. 10 mg EDCI, 4.5 mg HOBT, 5 mg acetylpiperazinyl and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed (eluent is ethyl acetate/petroleum ether/dichloromethane) (the volume ratio is 1:4:1), and then eluted to obtain 7 mg orange-yellow jelly.

Example 25

Preparation of gambogenic acyl cyclopropanamine $R^1$ is

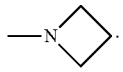

20 mg gambogenic acid and 0.5 ml dichloromethane were ice-bath cooled to 0° C. to form an ice-solution in a 10 ml reaction flask. 10 mg EDCI, 4.5 mg HOBT, 5 µl cyclopropanamine and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed (eluent is ethyl acetate/petroleum ether/) (the volume ratio is 1:8), and then eluted to obtain 5 mg orange-yellow jelly.

Example 26

Preparation of gambogenic acid (3-methoxy-pyrrolidine)

$R^1$ is

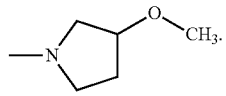

Referring to FIG. 3, 20 mg gambogenic acid and 0.5 ml dichloromethane were ice-bath cooled to 0° C. to form an ice-solution in a 10 ml reaction flask. 10 mg EDCI, 4.5 mg HOBT, 6 mg 3-methoxy-pyrrolidine and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed (eluent is ethyl acetate/petroleum ether/dichloromethane) (the volume ratio is 1:4:1), and then eluted to obtain 4 mg orange-yellow jelly.

Example 27

Preparation of gambogenic acid [3-(3-methoxy-pyrrolidine yl)-propyl]ester $R^1$ is

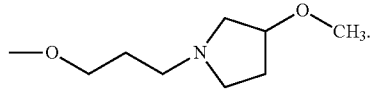

With reference to FIG. 3, 20 mg gambogenic acid and 0.5 ml dichloromethane were ice-bath cooled to 0° C. to form an ice-solution in a 10 ml reaction flask. 10 mg EDCI, 4.5 mg HOBT, 10 mg 3-(3-methoxy-pyrrolidine yl)-propanol and 0.5 ml dichloromethane were added into the ice-solution. The ice-solution was warmed naturally to room temperature and stirred to obtain a reaction solution.

After completion of the reaction, the reaction solution was diluted with 50 ml dichloromethane, and then washed with 0.5 M sulfuric acid aqueous solution, saturated saline, dried with anhydrous sodium sulfate, and then the solvent was evaporated, chromatographed (eluent is ethyl acetate/petroleum ether/dichloromethane) (the volume ratio is 1:4:1), and then eluted to obtain 7 mg orange-yellow jelly.

Example 28

Preparation of 10-methyl gambogenic acid $R^2$ and $R^3$ is H, R is methyl group in Formula (V).

With reference to FIG. 5, 24 mg magnesium, 1 ml ether and 0.07 ml iodomethane were dropwised into a 5 ml reaction flask, and maintaining micro-boiling to obtain a clear Grignard reagent. 100 mg cuprous iodide was dissolved in tetrahydrofuran to form a suspension, and then the suspension was cooled to $-40°$ C. and added 0.1 ml prepared Grignard reagent to form gray suspension.

20 mg gambogenic acid was added into tetrahydrofuran at $-20°$ C.

After completion of the reaction, 1 M hydrochloric acid quenched the reaction, ether extraction, and chromatographed separation to obtain 7 mg orange-yellow jelly.

The compounds synthesized from the present invention were studied by sulforhodamine B protein staining (sulfothodalnine B, SRB) and miceroculture tetrazolinetetrozohuln (MTT) colorimetric method respectively for in vitro anti-tumor activity (Cancer Res., 1988, 48 (3): 589).

The concentration gradient of the test compounds of the present invention is $10^{-4}$M, $10^{-5}$M, $10^{-6}$M, $10^{-7}$M, $10^{-8}$M, and the test compounds are 6-methoxy methyl ester gambogenic acid, ethyl ester gambogenic acid, 6-ethoxy ethyl ester gambogenic acid, 6-acyl gambogenic acid, piperidine gambogenic acid, diethylamide gambogenic acyl, morpholine gambogenic acid, and 12-hydroxy gambogenic acid, and 8,9-epoxy gambogenic acid. The test compounds and positive control gambogenic acid were diluted with dimethyl sulfoxide.

Inhibition rate(%)=[(control group OD value−administered group OD value)/control group OD value]×100%

Assessment of results:

Invalid: $10^{-5}$M inhibition rate<85%;
Weak: $10^{-5}$M inhibition rate≥85% or $10^{-6}$M>50%;
Potent: $10^{-6}$M inhibition rate≥75% or $10^{-7}$M inhibition rate>50%.

1. The Growth Inhibition of Tumor Cell Cal27

Human oral squamous cells carcinoma Cal27 were cultured in DMEM containing 10% fetal bovine serum (FBS), the cells with long-growth phase were forming suspension and culturing in 96-well plates. 10 µl test compounds of different concentrations as experimental group were added into each well of the 96-well plates. Blank control group received an equal volume containing the highest concentration of solvent (ie, $10^{-4}$M dimethyl sulfoxide) in DMEM. After incubation at 37° C. under 5% carbon dioxide conditions for 72 hours, the cells were fixed with trichloroacetic acid, and each well was added with 100 µl SRB solution, unbound SRB was washed away, and then OD values were measured at 550 nm by an automatic plate reader spectrophotometer. A tumor cell group without drugs is a blank control group. The growth inhibition rate of tumor cells was calculated and the results were as shown in Table 1.

TABLE 1 the growth inhibition of Cal27 tumor cell to the test compounds

| concentration | $10^{-4}$M | $10^{-5}$M | $10^{-6}$M | $10^{-7}$M | $10^{-8}$M | efficacy |
|---|---|---|---|---|---|---|
| gambogenic acid | 100 | 100 | 5 | 0 | 0 | invalid |
| 6-methoxy methyl ester gambogenic acid | 100 | 100 | 100 | 0 | 0 | potent |
| ethyl ester gambogenic acid | 100 | 100 | 98 | 0 | 0 | potent |
| 6-ethoxy ethyl ester gambogenic acid | 100 | 100 | 94 | 0 | 0 | potent |
| 6-acyl gambogenic acid | 100 | 100 | 96 | 0 | 0 | potent |
| piperidine gambogenic acid | 100 | 100 | 70 | 0 | 0 | invalid |
| diethylamide gambogenic acyl | 100 | 100 | 100 | 23 | 0 | potent |
| morpholine gambogenic acid | 100 | 100 | 100 | 14 | 0 | potent |
| 12-hydroxy gambogenic acid | 100 | 100 | 100 | 0 | 0 | potent |
| 8,9-epoxy gambogenic acid | 100 | 100 | 100 | 0 | 0 | potent |

TABLE 2 the growth inhibition rate of tumor cells MCF-7 to the test compounds

| concentration | $10^{-4}$M | $10^{-5}$M | $10^{-6}$M | $10^{-7}$M | $10^{-8}$M | efficacy |
|---|---|---|---|---|---|---|
| gambogenic acid | 100 | 100 | 0 | 0 | 0 | invalid |
| 6-methoxy methyl ester gambogenic acid | 100 | 100 | 80 | 0 | 0 | potent |
| ethyl ester gambogenic acid | 100 | 100 | 96 | 0 | 0 | potent |
| 6-ethoxy ethyl ester gambogenic acid | 100 | 100 | 86 | 0 | 0 | potent |
| 6-acyl gambogenic acid | 100 | 100 | 83 | 0 | 0 | potent |
| piperidine gambogenic acid | 100 | 100 | 67 | 0 | 0 | invalid |
| diethylamide gambogenic acyl | 100 | 100 | 84 | 0 | 0 | potent |

TABLE 2-continued the growth inhibition rate of tumor cells MCF-7 to the test compounds

| concentration | $10^{-4}$M | $10^{-5}$M | $10^{-6}$M | $10^{-7}$M | $10^{-8}$M | efficacy |
|---|---|---|---|---|---|---|
| morpholine gambogenic acid | 100 | 100 | 78 | 14 | 0 | potent |
| 12-hydroxy gambogenic acid | 100 | 100 | 82 | 0 | 0 | potent |
| 8,9-epoxy gambogenic acid | 100 | 100 | 80 | 0 | 0 | potent |

2. The Growth Inhibition of Tumor Cell MCF-7

Human breast cancer cells MCF-7 were cultured in DMEM containing 10% FBS, the cell with long-growth phase was formed into suspension and cultured in 96-well plates. The test compounds as experimental group with different concentrations were added into each well of the 96-well plates. Blank control group received an equal volume containing the highest concentration of solvent (ie, $10^{-4}$M dimethyl sulfoxide) in DMEM. After incubation at 37° C. under 5% carbon dioxide conditions for 72 hours, each well was added with MTT to 1 mg/ml final concentration for incubation for 4 hours. The supernatant solution in each well was aspirated and added with 200 μl DMSO to dissolve crystals, and then OD values were measured at 490 nm by an automatic plate reader spectrophotometer. A tumor cell group without drugs is a blank control group. The growth inhibition rates of tumor cells were calculated and the results were as shown in Table 2.

Accordingly, Tables 1 and 2 of the present invention indicate that gambogenic acid derivatives have a stronger growth inhibition of tumor cell.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the claims.

The invention claimed is:

1. A gambogenic acid derivative of Formula (I) or Formula (II) as follows:

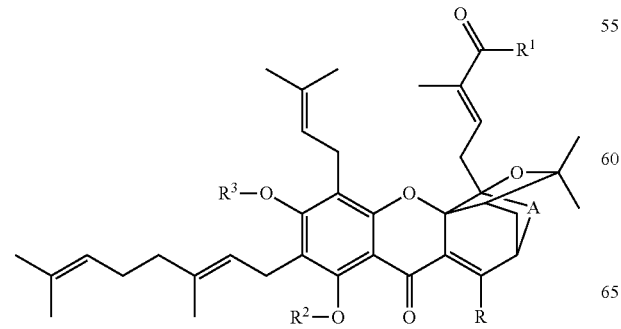

Formula (I)

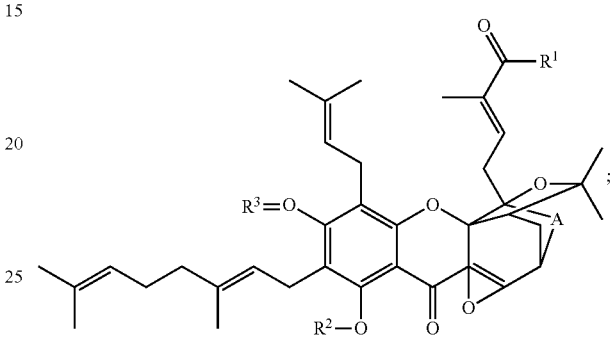

Formula (II)

wherein:

A is —CO— or —HC(OH)—;

$R^2$ is selected from any one of the groups as follows: hydrogen, straight chain or branched chain $C_1$ to $C_{10}$ alkyl group, $C_3$ to $C_8$ cycloalkyl group, aromatic group or aromatic group substituted by $C_1$ to $C_{10}$ alkyl, heteroaryl group, and acyl group substituted by $C_1$ to $C_{10}$ alkyl or acyl group substituted by aromatic group;

$R^3$ is selected from any one of the groups as follows: hydrogen, acyl group substituted by $C_1$ to $C_{10}$ alkyl or aryl group substituted by aromatic group;

R is selected from any one of the groups as follows: hydrogen, straight chain or branched chain $C_1$ to $C_{10}$ alkyl group, $C_3$ to $C_8$ cycloalkyl group, straight chain or branched chain $C_2$ to $C_{10}$ alkenyl group or $C_3$ to $C_8$ cycloalkenyl group, phenyl group or phenyl group substituted by $C_1$ to $C_{10}$ alkyl group, $C_2$ to $C_6$ alkynyl group, nucleophiles containing secondary amine group including straight chain or branched chain alkyl amino group, straight chain or branched chain alkenyl amino group; aromatic or aromatic alkylamino group, the amine obtained by addition of chain alkynyl amine group and α, β-unsaturated ketones;

$R^1$ is selected from:

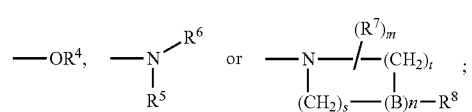

wherein $R^4$ is selected from the group consisting of any one of the following: hydrogen, straight chain or branched chain $C_1$ to $C_{10}$ alkyl group, or alkyl group containing optionally 1 to 3 substituted groups including oxygen group, halogen, $C_1$ to $C_{10}$ alkoxy group, acyloxy group, $C_1$ to $C_{10}$ alkoxycarbonyl group, aryloxy group; $C_3$-$C_8$ cycloalkyl group, $C_1$ to $C_{10}$ alkyl group substituted by 1, 2 or 3 heteroatoms; alkylaryl group including $C_1$ to $C_{10}$ alkyl group substituted by aromatic group and $C_1$ to $C_{10}$ alkyl group optionally substituted by 1 to 3 substituted aromatic groups including acyl group, —$OCH_2O$—, halogen, haloalkyl group, aryl group, $C_3$ to $C_8$ cycloalkyl group, $C_1$ to $C_{10}$ alkyl group, hydroxyl group, acyloxy group, $C_1$ to $C_{10}$ alkoxy group; heteroarylalkyl group including $C_1$ to $C_{10}$ alkoxy group substituted by heteroaryl group, and $C_1$ to $C_{10}$ alkyl group optionally substituted by any heteroaryl group including heteroaryl group, $C_1$ to $C_{10}$ alkyl group, aralkyl group, $C_3$ to $C_8$ cycloalkyl group, $C_1$ to $C_{10}$ alkoxycarbonyl group, carbamoyl group, aromatic group and $C_1$ to $C_6$ amide group; straight chain or branched chain $C_2$ to $C_{10}$ alkenyl group or alkenyl group including optionally 1 to 3 substituted groups including oxygen group, halogen, aromatic ring group, aralkyl group, $C_1$ to $C_{10}$ alkoxy group, acyloxy group, amide group, $C_1$ to $C_6$ amine acyl group, $C_1$ to $C_{10}$ alkoxy group and $C_1$ to $C_{10}$ heteroalkyl group including 1, 2 or 3 heteroatoms; $C_4$ to $C_{10}$ cycloalkenyl, $C_4$ to $C_{10}$ alkynyl group, or alkynyl group including optionally 1 to 3 substituted group including oxygen group, halogen, aromatic ring group, aralkyl group, $C_1$ to $C_{10}$ alkoxy group, acyloxy group, amide group, $C_1$ to $C_6$ acyl group, $C_1$ to $C_{10}$ alkoxy group, aryloxy group and $C_1$ to $C_{10}$ heteroalkyl group including optionally 1, 2 or 3 heteroatoms;

$R^5$ and $R^6$ are independently selected from any one of the groups as follows: hydrogen; straight chain or branched $C_1$ to $C_{10}$ alkyl group or $C_1$ to $C_{10}$ alkyl group containing optionally 1 to 3 substituted groups including oxygen group, halogen, $C_1$ to $C_{10}$ alkoxy group, acyloxy group, $C_1$ to $C_{10}$ alkoxyacyl group, aryloxy group; $C_3$ to $C_8$ cycloalkyl group; $C_1$ to $C_{10}$ alkyl group substituted by 1, 2 or 3 heteroatoms; alkylaryl group including $C_1$ to $C_{10}$ alkyl group substituted by aromatic group and $C_1$ to $C_{10}$ alkyl group substituted by optionally 1 to 3 substituted aromatic groups including acyl group, —$OCH_2O$—, halogen, haloalkyl group, hydroxyl group, aryl group, $C_3$ to $C_8$ cycloalkyl group, $C_1$ to $C_{10}$ alkyl group, acyloxy group, $C_1$ to $C_{10}$ alkoxy group; heteroarylalkyl group includes $C_1$ to $C_{10}$ alkoxy group substituted by heteroaryl group, and $C_1$ to $C_{10}$ alkyl group optionally substituted by any heteroaryl group including heteroaryl group, $C_1$ to $C_{10}$ alkyl group, aralkyl group, $C_3$ to $C_8$ cycloalkyl group, $C_1$ to $C_{10}$ alkoxycarbonyl group, carbamoyl group, aromatic group and $C_1$ to $C_6$ amide group; straight chain or branched $C_2$ to $C_{10}$ alkenyl group or alkenyl group containing optionally 1 to 3 substituted groups including oxygen group, halogen, aromatic ring group, aralkyl group, $C_1$ to $C_{10}$ alkoxy group, acyloxy group, amide group, $C_1$ to $C_6$ amine acyl group, $C_1$ to $C_{10}$ alkoxy group, aryloxy group, and $C_1$ to $C_{10}$ heteroalkyl group containing 1, 2 or 3 heteroatoms; $C_4$ to $C_{10}$ cycloalkenyl, $C_4$ to $C_{10}$ alkynyl group, or alkynyl group containing optionally 1 to 3 substituted groups including oxygen group, halogen, aromatic ring group, aralkyl group, $C_1$ to $C_{10}$ alkoxy group, acyloxy group, amide group, $C_1$ to $C_6$ acyl group, $C_1$ to $C_{10}$ alkoxy group, aryloxy group and $C_1$ to $C_{10}$ heteroalkyl group including 1, 2 or 3 heteroatoms;

s and t are positive integers, and the sum of s and t is a natural number of 2 to 10;

m is 0, 1, 2 or 3, and represents the number of the substituted group on $R^7$ of the ring;

n is 0, 1, 2 or 3, and represents the number of B on the ring; B is carbon, nitrogen or oxygen;

B is carbon, the groups of $R^7$, $R^8$ are identical with the group of $R^5$, or carbonyl group, imino group, oxime group, aliphatic group; or when B is tertiary nitrogen, $R^8$ is oxygen, and so as to form nitrogen oxides with B; and, $R^4$, $R^3$, $R^2$, $R^1$ are not simultaneously hydrogen on the Formula (I).

2. The gambogenic acid derivative as claimed in claim 1, wherein said gambogenic acid derivative is represented by Formula (III), Formula (IV) or Formula (V) as follows:

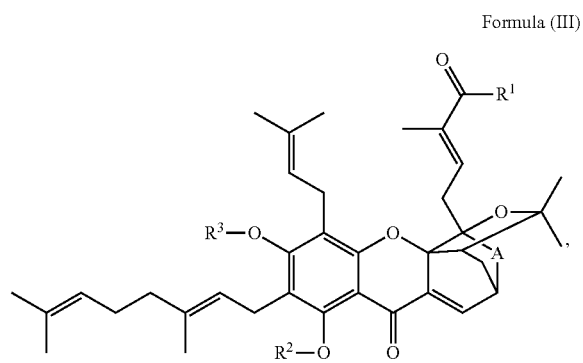

Formula (III)

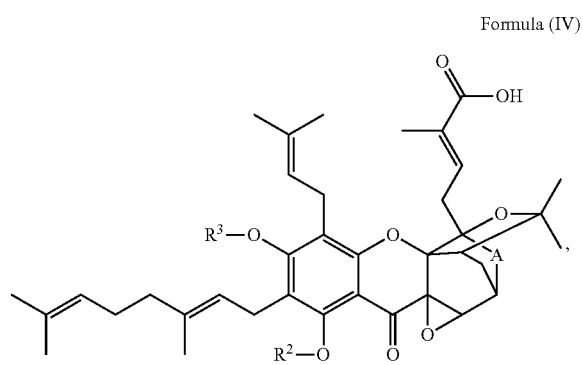

Formula (IV)

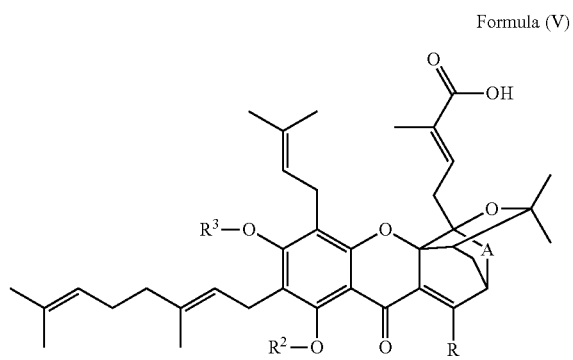

Formula (V)

wherein $R^2$, $R^3$, $R^4$ are not simultaneously hydrogen on Formula (III); R, $R^2$, $R^3$ are not simultaneously hydrogen on Formula (V).

3. The gambogenic acid derivative as claimed in claim 1, wherein $R^4$ is selected from the group consisting of any one of the groups as follows: hydrogen, methyl group, ethyl group, propyl group, isopropyl group, butyl group, isobutyl group, tert-butyl group, hexyl group, octyl group, $C_1$ to $C_{10}$ alkyl group optionally substituted by 1 to 3 substituted groups including any of oxygen group, halogen, $C_1$ to $C_{10}$ alkoxy group, acyloxy group, $C_1$ to $C_{10}$ alkoxyacyl group, aromatic group; cyclohexyl group, cyclopentyl group; cyclopropyl group, $-CH_2CH_2OCH_2CH_3$, $-CH_2CH_2OCH_2CH_2OCH_2CH_3$, $-CH_2CH_2NHCH_3$, $-OCH_2O-$, halogen, haloalkyl group, hydroxyl group, $-CH_2CH_2N(CH_2CH_3)_2$, $-CH_2CH_2OCH_2CH_2NCH_3$, benzyl group, phenethyl group, phenylpropyl group, tetrahydro-pyrrolyl group, piperidinyl group, morpholinyl group, $-CH_2CH_2OCH_2CH_2OCH_2NHCH_3$, $-CH_2CH_2NHCH_2CH_3$, $-CH_2$(N-ethyl-pyrrolidine), $-CH_2C(CH_3)CH_2N(CH_3)$, $C_1$ to $C_{10}$ alkyl group substituted by optionally 1 to 3 substituted aromatic groups including acyl group, aryl group, $C_3$ to $C_8$ cycloalkyl group, $C_1$ to $C_{10}$ alkyl group, hydroxyl group, acyloxy group, $C_1$ to $C_{10}$ alkoxy group; heteroarylalkyl group including $C_1$ to $C_{10}$ alkoxy group substituted by heteroaryl group, and $C_1$ to $C_{10}$ alkyl group optionally substituted by any heteroaryl group including heteroaryl group, $C_1$ to $C_{10}$ alkyl group, aralkyl group, $C_3$ to $C_8$ cycloalkyl group, $C_1$ to $C_{10}$ alkoxycarbonyl group, carbamoyl group, aromatic group and $C_1$ to $C_6$ amide group; straight chain or branched chain $C_2$ to $C_{10}$ alkenyl group or alkenyl group containing optionally 1 to 3 substituted groups including oxygen group, halogen, aromatic ring group, aralkyl group, $C_1$ to $C_{10}$ alkoxy group, acyloxy group, amide group, $C_1$ to $C_6$ amine acyl group, $C_1$ to $C_{10}$ alkoxy group, aryloxy group, and $C_1$ to $C_{10}$ heteroalkyl group containing 1, 2 or 3 heteroatoms; $C_4$ to $C_{10}$ cycloalkenyl, $C_4$ to $C_{10}$ alkynyl group, or $C_4$ to $C_{10}$ alkynyl group containing optionally 1 to 3 substituted groups including oxygen group, halogen, aromatic ring group, aralkyl group, $C_1$ to $C_{10}$ alkoxy group, acyloxy group, amide group, $C_1$ to $C_6$ amine acyl group, $C_1$ to $C_{10}$ alkoxy group, aryloxy group and $C_1$ to $C_{10}$ heteroalkyl group containing 1, 2 or 3 heteroatoms.

4. The gambogenic acid derivative as claimed in claim 1, wherein $R^5$ and $R^6$ are independently selected from any one of the groups as follows: hydrogen, methyl group, ethyl group, propyl group, isopropyl group, butyl group, isobutyl butyl group, tert-butyl group, hexyl group, octyl group; $C_1$ to $C_{10}$ alkyl group containing optionally 1 to 3 substituted groups including hydroxyl group, amino group, $C_1$ to $C_{10}$ alkylamino group, oxygen group, halogen, $C_1$ to $C_{10}$ alkoxy group, acyloxy group, $C_1$ to $C_{10}$ alkoxyacyl group, aryloxy group; cyclohexyl group, cyclopentyl group, cyclopropyl group, $-CH_2CH_2OCH_2CH_3$, $-CH_2CH_2OCH_2CH_2OCH_2CH_3$, $-CH_2CH_2NHCH_3$, $-CH_2CH_2N(CH_2CH_3)_2$, $-CH_2CH_2OCH_2CH_2NCH_3$, $-CH_2$(N-ethyl-pyrrolidine), tetrahydro-pyrrolyl group, piperidinyl group, morpholinyl group, benzyl group, $-CH_2CH_2OCH_2CH_2OCH_2NHCH_3$, $-CH_2CH_2NHCH_2CH_3$, phenethyl group, phenylpropyl group, $-CH_2C(CH_3)CH_2N(CH_3)$; $C_1$ to $C_{10}$ alkyl group optionally substituted by 1 to 3 substituted aromatic groups including acyl group, $-OCH_2O-$, halogen, haloalkyl group, aryl group, $C_3$ to $C_8$ cycloalkyl group, $C_1$ to $C_{10}$ alkyl group, hydroxyl group, acyloxy group, $C_1$ to $C_{10}$ alkoxy group; heteroarylalkyl group including $C_1$ to $C_{10}$ alkoxy group substituted by heteroaryl group, and $C_1$ to $C_{10}$ alkyl group optionally substituted by any heteroaryl group including heteroaryl group, $C_1$ to $C_{10}$ alkyl group, aralkyl group, $C_3$ to $C_8$ cycloalkyl group, $C_1$ to $C_{10}$ alkoxycarbonyl group, carbamoyl group, aromatic group and $C_1$ to $C_6$ amide acyl group, straight chain or branched chain $C_1$ to $C_{10}$ alkenyl group or alkynyl group containing optionally 1 to 3 substituted groups including oxygen group, halogen, aromatic ring group, aralkyl group, $C_1$ to $C_{10}$ alkoxy group, acyloxy group, amide group, $C_1$ to $C_6$ amine acyl group, $C_1$ to $C_{10}$ alkoxy group, aryloxy group and $C_1$ to $C_{10}$ heteroalkyl group containing 1, 2 or 3 heteroatoms; $C_4$ to $C_{10}$ cycloalkenyl, $C_4$ to $C_{10}$ alkynyl group, or $C_4$ to $C_{10}$ alkynyl group containing optionally 1 to 3 substituted groups including oxygen group, halogen, aromatic ring group, aralkyl group, $C_1$ to $C_{10}$ alkoxy group, acyloxy group, amide group, $C_1$ to $C_6$ amine acyl group, $C_1$ to $C_{10}$ alkoxy group, acyloxy group, and $C_1$ to $C_{10}$ heteroalkyl group containing 1, 2 or 3 heteroatoms.

5. The gambogenic acid derivative as claimed in claim 1, wherein $R^3$ is selected from any one of the groups as follows: hydrogen, formyl group, acetyl group, carbamoyl group, phenyl group, benzyl group, and phenylacetyl group.

6. The gambogenic acid derivative as claimed in claim 1, wherein $R^2$ is selected from any one of groups as follows: hydrogen, methyl group, ethyl group, propyl group, isopropyl group, butyl group, isobutyl group, tert-butyl group, hexyl group, octyl group, cyclopropyl group, cyclobutyl group, cyclopentyl group, cyclohexyl group, cycloheptyl group, benzyl group, phenethyl group, furyl group, pyranyl group, 2H-pyrrolyl group, pyrrolyl group, imidazolyl group, pyrazolyl group, pyridyl group, formyl group, acetyl group, carbamoyl acyl group, phenyl group, benzyl group, and phenylacetyl group.

7. The gambogenic acid derivative as claimed in claim 1, wherein R is selected from any one of groups as follows: methyl group, ethyl group, propyl group, isopropyl group, butyl group, isobutyl group, tert-butyl group, hexyl group, octyl group, cyclohexyl group, cyclopentyl group, vinyl group, butene group, hexenyl group, cyclohexenyl group, cyclopentenyl group, phenyl group, benzyl group, phenethyl group, phenylpropyl group, butynyl group, hexynyl group, morpholinyl group, piperidinyl group, and piperazinyl group.

8. The gambogenic acid derivative as claimed in claim 1, wherein $R^1$ is selected from:

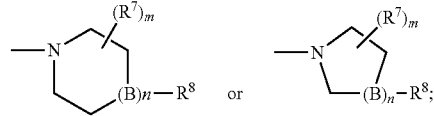

wherein $R^7$ is selected from any one of the following groups:

substituted group as defined in $R^5$, carbonyl group; imino group, oxime group, aliphatic group;

m, n is 0, 1, 2 or 3;

B is carbon, nitrogen or oxygen;

the group of $R^8$ is identical with $R^5$, or is oxygen so as to form nitrogen oxides with B.

9. A salt of gambogenic acid derivatives as claimed in claim 1, wherein the salt is with inorganic acid, organic acid, inorganic base or organic base.

10. A method for preparing a gambogenic acid derivative, the method comprising introducing $R^2$ and $R^3$ to the gambogenic acid or gambogenic acid derivative of Formula (VI)

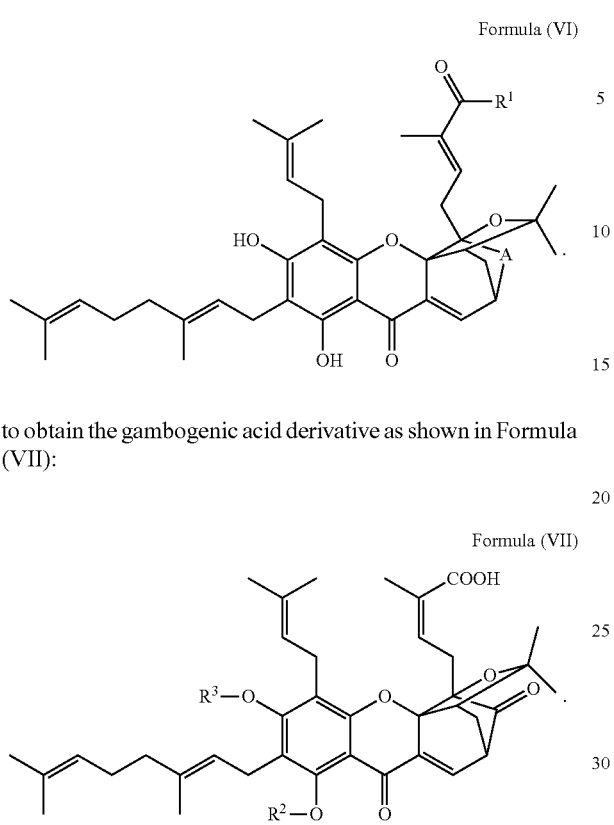

Formula (VI)

to obtain the gambogenic acid derivative as shown in Formula (VII):

Formula (VII)

11. A method for preparing a gambogenic acid derivative, the method comprising reducing the carbonyl group of $C_6$ carbon to obtain a gambogenic acid derivative as shown in Formula (VIII), and/or by esterification or acidification with $R^4OH$, $R^5R^6NH$ or

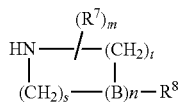

to obtain a gambogenic acid derivative as shown in Formula (III).

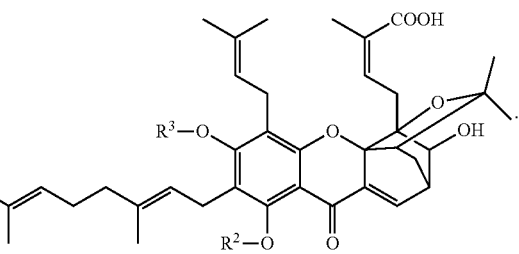

Formula (VIII)

12. A method for preparing a gambogenic acid derivative, the method comprising using the gambogenic acid, the gambogenic acid derivative as shown in Formula (VII), or the gambogenic acid derivative as shown in Formula (VIII) as raw material; and oxidizing the double bond between $C_9$ and $C_{10}$ by peroxidant in alkaline condition to obtain a gambogenic acid derivative as shown in Formula (II).

13. A method for preparing a gambogenic acid derivative, the method comprising preparing the gambogenic acid derivative as shown in Formula (I) by 1,4-addition on double bond between the $C_9$ and $C_{10}$ using organic copper reagent RCu with the gambogenic acid, the gambogenic acid derivative as shown in Formula (VII), or gambogenic acid derivative as shown in Formula (VIIII).

14. An anticancer drug comprising an active ingredient of a gambogenic acid derivative as claimed in claim 1.

* * * * *